United States Patent
Pardee et al.

(10) Patent No.: US 12,215,370 B2
(45) Date of Patent: Feb. 4, 2025

(54) METHODS FOR DETECTING TARGET ANALYTES USING SYNTHETIC BIOLOGICAL CIRCUITS THAT MODIFY GLUCOSE LEVELS IN A CELL-FREE SYSTEM

(71) Applicant: The Governing Council of the University of Toronto, Toronto (CA)

(72) Inventors: Keith Pardee, Toronto (CA); Evan Amalfitano, Oakville (CA); Margot Karlikow, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 28 days.

(21) Appl. No.: 16/956,431

(22) PCT Filed: Dec. 21, 2018

(86) PCT No.: PCT/CA2018/051646
§ 371 (c)(1),
(2) Date: Jun. 19, 2020

(87) PCT Pub. No.: WO2019/119148
PCT Pub. Date: Jun. 27, 2019

(65) Prior Publication Data
US 2020/0318148 A1 Oct. 8, 2020

Related U.S. Application Data

(60) Provisional application No. 62/609,525, filed on Dec. 22, 2017.

(51) Int. Cl.
*C12P 19/02* (2006.01)
*C12P 19/14* (2006.01)
*C12Q 1/54* (2006.01)

(52) U.S. Cl.
CPC .............. *C12P 19/02* (2013.01); *C12P 19/14* (2013.01); *C12Q 1/54* (2013.01); *C12Y 101/01047* (2013.01); *C12Y 301/03009* (2013.01); *C12Y 302/01001* (2013.01); *C12Y 302/0102* (2013.01); *C12Y 302/01021* (2013.01); *C12Y 302/01023* (2013.01); *C12Y 302/01026* (2013.01); *C12Y 302/01028* (2013.01)

(58) Field of Classification Search
None
See application file for complete search history.

(56) References Cited

U.S. PATENT DOCUMENTS

| | | | |
|---|---|---|---|
| 8,945,943 B2 | 2/2015 | Lu et al. | |
| 2016/0076083 A1* | 3/2016 | Ellington | C12Q 1/6897 435/6.12 |
| 2016/0252515 A1 | 9/2016 | Lu et al. | |
| 2018/0334731 A1* | 11/2018 | Pardee | C12Q 1/6897 |

FOREIGN PATENT DOCUMENTS

| | | |
|---|---|---|
| CN | 103025885 A | 4/2013 |
| CN | 104968786 A | 10/2015 |
| CN | 106232832 A | 12/2016 |
| CN | 111630178 A | 9/2020 |
| JP | 2015533297 A | 11/2015 |
| WO | 2011150186 A1 | 12/2011 |
| WO | 2014074648 A1 | 5/2014 |
| WO | 2015085209 A1 | 6/2015 |
| WO | 2017205668 A1 | 11/2017 |
| WO | 2018039802 A1 | 3/2018 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Gu, C., et al., "Portable Detection of Melamine in Milk Using a Personal Glucose Meter Based on an in Vitro Selected Structure-Switching Aptamer." Analytical Chemistry, 2015, 87, 7676-7682.
Wang, Q., et al., "Sensitive point-of-care monitoring of cardiac biomarker myoglobin using aptamer and ubiquitous personal glucose meter." Biosensors and Bioelectronics, 2015, 64, 161-164.
Wu, T., et al., "Bioinspired DNA—Inorganic Hybrid Nanoflowers Combined with a Personal Glucose Meter for Onsite Detection of miRNA." ACS Appl. Mater. Interfaces, 2018, 10, 42050-42057.
Yan, L., et al., "Target-Responsive "Sweet" Hydrogel with Glucometer Readout for Portable and Quantitative Detection of Non-Glucose Targets." J. Am. Chem. Soc., 2013, 135, 3748-3751.
Yang, W., et al., "Portable and sensitive detection of protein kinase activity by using commercial personal glucose meter." Sensors and Actuators B, 2015, 210, 508-512.
Zhu, X., et al., "Biosensing of DNa oxidative damage: a model of using glucose meter for non-glucose biomarker detection." International Journal of Nanomedicine, 2017, 12, 979-987.
Zou, Y., et al., "Nucleic acid purification from plants, animals and microbes in under 30 seconds." PLOS Biology, 2017, 1-22.
Lan, T., et al., "Transforming the blood glucose meter into a general healthcare meter for in vitro diagnostics in mobile health." Biotechnol Adv., 2016, 34(3), 331-341.
Roelof Van Der Meer, J., and Belkin, S., "Where microbiology meets microengineering: design and applications of reporter bacteria." Nature Reviews, Mircobiology, 2010, 8, 511-522.

(Continued)

*Primary Examiner* — Christian L Fronda
(74) *Attorney, Agent, or Firm* — SMART & BIGGAR LP; Ainslie Parsons

(57) ABSTRACT

Described are methods for generating a reporter molecule in response to a target analyte in a cell-free system. A synthetic biological circuit is used to modify the level of the reporter molecule in response to the presence of the target analyte. The reporter molecule may be glucose or another molecule readily detected using a device such as glucose monitor or other portable sensor. Also provided are kits comprising a cell-free system with a synthetic biological circuit that generates or consumes a reporter molecule in response to a target analyte.

5 Claims, 14 Drawing Sheets

Specification includes a Sequence Listing.

(56) References Cited

OTHER PUBLICATIONS

Pardee, K., et al., "Paper-Based Synthetic Gene Networks." Cell, 2014, 159, 940-954.
Pardee, K., et al., "Rapid, Low-Cost Detection of Zika Virus Using Programmable Biomolecular Components." Cell, 2016, 165, 1-12.
Reis, A.T., et al., "Extraction of mercury water-soluble fraction from soils: An optimization study." Geoderma, 2014, 213, 255-260.
Reyes, L.H., et al., "Robust microwave-assisted extraction protocol for determination of total mercury and methylmercury in fish tissues." Analytica Chimica Acta, 2009, 121-128.
Su, J., et al., "Personal glucose sensor for point-of-care early cancer diagnosis." Chem. Commun., 2012, 48, 6909-6911.
Su, J., et al., "Sensitive detection of copper(II) by a commercial glucometer using click chemistry." Biosensors and Bioelectronics, 2013, 45, 219-222.
Wang, Q., et al., "Multiplex detection of nucleic acids using a low cost microfluidic chip and a personal glucose meter at the point-of-care." Chem. Commun., 2014, 50, 3824-3826.
Wedekind, J.E., et al., "Metalloriboswitches: RNA-based inorganic ion sensors that regulate genes." J. Biol. Chem., 2017, 292(23) 9441-9450.
Xiang, Y., and Lu, Y., "Using personal glucose meters and functional DNA sensors to quantify a variety of analytical targets." Nature Chemistry, 2011, 3, 697-703.
Xiang, Y., and Lu, Y., "Using Commercially Available Personal Glucose Meters for Portable Quantification of DNA." Analytical Chemistry, 2012, 84, 1975-1980.
Xiang, Y., and Lu, Y., "An invasive DNA approach toward a general method for portable quantification of metal ions using a personal glucose meter†‡." Chem. Commun., 2013, 49, 585-587.
Zhang, X., et al., "Electrochemical Assay to Detect Influenza Viruses and Measure Drug Susceptibility." Angew Chem Int Ed Engl. May 11, 2015; 54(20): 5929-5932.
Written Opinion completed Mar. 17, 2019 and International Search Report completed Feb. 28, 2019 for corresponding PCT application No. PCT/CA2018/051646.
Drikic, M., and De Buck, J., "Split trehalase as a versatile reporter for a wide range of biological analytes." Biotechnol. Bioeng., 2018, 116, 5, 1128-1136.
Yan, L., et al., "Isothermal amplified detection of DNA and RNA." Mol. BioSyst., 2014. 10, 970-1003.
Green, A.A., et al., "Toehold switches: de-novo-designed regulators of gene expression." Cell, 2014, 159, 925-939.
Zhou, W., et al., "Metal Sensing by DNS." Chem. Rev., 2017, 117, 8272-8325.
Supplementary European Search Report, in connection to corresponding EP application No. 18891931.0, dated Jul. 14, 2021.
An Office Action which issued in connection to corresponding Chinese patent application No. 2018800871297 dated Nov. 22, 2023, 3 pages.

* cited by examiner

A

B

C

SEQUENCE LISTING

```
<160> NUMBER OF SEQ ID NOS: 4

<210> SEQ ID NO 1
<211> LENGTH: 1730
<212> TYPE: DNA
<213> ORGANISM: Artificial Sequence
<220> FEATURE:
<223> OTHER INFORMATION: Synthetic

<400> SEQUENCE: 1
taatacgact cactataggg atctattact acttaccatt gtcttgctct atacagaaac      60
agaggagata tagaatgaga caatggaacc tggcggcagc gcaaaagatg cgtaaagatt     120
ataaagatga tgatgataaa ggacatcatc atcatcatca cagcagcggc gagaacctgt     180
acttccaatc ctctggaggt gggggttctg gaacagcggt acggatagat tatgcaagcg     240
ggttaactga tcgcgaaaac tctatgttca aagaaatcca gttgtcaggc gttttgccg     300 attcaaaaac ctttgtggat agccatccca aattgccct ggcggaaatc gccgagcttt     360
accatgtccg gcaacagcag gcgggttttg acctcgccgc ttttgttcac cggtattttg     420
agctgccgcc gagcattgcc tccggttttg tcagcgatac ctcgcgcccg gtggaaaagc     480
atatcgacat tctctgggat gtgctcaccc gccaaccgga caggcaggag gcgggaaccc     540
tgctgccctt accttacccc tatgtcgttc ccggcggccg cttccgcgaa atttactact     600
gggacagcta tttcaccatg ctcggtttgc aggcatcgaa gcgctgggat ctgatggagg     660
gtatggtgaa taatttttca cacctgatcg acaccatcgg ctttattccc aacggcaatc     720
gcacctatta cgagggccgc tcccagccgc cttttacgc cctgatggtg gagttgctgg     780
ccaataaaca gggtgagtcg gtgctgctcg cgcatttgcc gcatttgcgc agggaatatg     840
aattctggat ggagggcgcc gctaaacttt cgcccgctgc acccgcgcat cgccgtgtgg     900
```

```
tgctgctgcc ggatggcagc atactcaatc gctactggga tgatatagcc gcgccgcgcc    960
cggaatcctt ccgcgaagac tacgaactgg cggaagccat cggcggcaac aagcgcgagc   1020
tgtaccgcca tattcgcgcg gcggcagaat ccggctggga cttcagcagc cgctggttca   1080
aagatggcaa tggcatggcc agcatccaca ccaccgatat tatcccggtg gatttgaatg   1140
cgctggtctt taacctggag cggatgctgg cccatattta tggcttgcag ggcgaccagg   1200
atcaggccac gcattactac caattggcgg agcagcgcaa acaggcgttg ctgcgctact   1260
gttggaatgc gcagcaggga ttttccacg attacgatta tgtcgccgca caacagacgc    1320
cggtcatgtc gctggcggcg gtttacccgc tttatttcag tatggtcgac cagcgcacgg   1380
gcgaccgggt cgccgaacag atagaggcgc attttatcca ggcgggcggt gtgaccacga   1440
ccctggcgac cacaggccag cagtgggacg cgcccaatgg ctgggcgccg ctgcaatggc   1500
tgaccatcca gggcctgcgc aattatcacc acaattcagc ggcggagcag atcaaacagc   1560
gctggattgc actcaaccag cgcgtttacc gcaacaccgg aaagttggtg gaaaaataca   1620
acgtctatga cctggatgtg gccggcggcg gtggcgaata tgaattacag gatggcttcg   1680
gttggaccaa cggtgtcttg ttgcacttac tcaacgaaag tacaccctaa               1730

<210> SEQ ID NO 2
<211> LENGTH: 65
<212> TYPE: RNA
<213> ORGANISM: Artificial Sequene
<220> FEATURE:
<223> OTHER INFORMATION: Synthetic

<400> SEQUENCE: 2
gggugauggg acauuccgau gucccaucaa uaagagcaag acaaugguaa guaguaauag     60
auaag                                                                65

<210> SEQ ID NO 3
<211> LENGTH: 3191
<212> TYPE: DNA
<213> ORGANISM: Artificial Sequence
<220> FEATURE:
<223> OTHER INFORMATION: Synthetic

<400> SEQUENCE: 3
taatacgact cactataggg agtttgatta cattgtcgtt tagtttagtg atacataaac     60
agaggagata tcacatgact aaacgaaacc tggcggcagc gcaaagatg cgtaaaatga    120 ccatgattac ggattcactg gccgtcgttt tacaacgtcg tgactgggaa aaccctggcg    180
ttacccaact taatcgcctt gcagcacatc cccctttcgc cagctggcgt aatagcgaag    240
aggcccgcac cgatcgccct tcccaacagt tgcgcagcct gaatggcgaa tggcgctttg    300
cctggtttcc ggcaccagaa gcggtgccgg aaagctggct ggagtgcgat cttcctgagg    360
ccgatactgt cgtcgtcccc tcaaactggc agatgcacgg ttacgatgcg cccatctaca    420
ccaacgtgac ctatcccatt acggtcaatc cgccgtttgt tcccacggag aatccgacgg    480
gttgttactc gctcacattt aatgttgatg aaagctggct acaggaaggc cagacgcgaa    540 ttattttga tggcgttaac tcggcgtttc atctgtggtg caacgggcgc tgggtcggtt    600
acggccagga cagtcgtttg ccgtctgaat ttgacctgag cgcatttta cgcgccggag    660 aaaaccgcct cgcggtgatg gtgctgcgct ggagtgacgg cagttatctg gaagatcagg    720
atatgtggcg gatgagcggc attttccgtg acgtctcgtt gctgcataaa ccgactacac    780
```

```
aaatcagcga tttccatgtt gccactcgct ttaatgatga tttcagccgc gctgtactgg    840
aggctgaagt tcagatgtgc ggcgagttgc gtgactacct acgggtaaca gtttctttat    900
ggcagggtga aacgcaggtc gccagcggca ccgcgccttt cggcggtgaa attatcgatg    960
agcgtggtgg ttatgccgat cgcgtcacac tacgtctgaa cgtcgaaaac ccgaaactgt   1020
ggagcgccga atcccgaatc tctatcgtgc ggtggttgaa actgcacacc gccgacggca   1080
cgctgattga agcagaagcc tgcgatgtcg gtttccgcga ggtgcggatt gaaaatggtc   1140
tgctgctgct gaacggcaag ccgttgctga ttcgaggcgt taaccgtcac gagcatcatc   1200
ctctgcatgg tcaggtcatg gatgagcaga cgatggtgca ggatatcctg ctgatgaagc   1260
agaacaactt taacgccgtg cgctgttcgc attatccgaa ccatccgctg tggtacacgc   1320
tgtgcgaccg ctacggcctg tatgtggtgg atgaagccaa tattgaaacc cacggcatgg   1380
tgccaatgaa tcgtctgacc gatgatccgc gctggctacc ggcgatgagc gaacgcgtaa   1440
cgcgaatggt gcagcgcgat cgtaatcacc cgagtgtgat catctggtcg ctggggaatg   1500
aatcaggcca cggcgctaat cacgacgcgc tgtatcgctg gatcaaatct gtcgatcctt   1560
cccgcccggt gcagtatgaa ggcggcggag ccgacaccac ggccaccgat attatttgcc   1620
cgatgtacgc gcgcgtggat gaagaccagc ccttcccggc tgtgccgaaa tggtccatca   1680
aaaaatggct ttcgctacct ggagagacgc gcccgctgat cctttgcgaa tacgcccacg   1740
cgatgggtaa cagtcttggc ggtttcgcta aatactggca ggcgtttcgt cagtatcccc   1800
gtttacaggg cggcttcgtc tgggactggg tggatcagtc gctgattaaa tatgatgaaa   1860
acggcaaccc gtggtcggct tacgcgcgtg attttggcga tacgccgaac gatcgccagt   1920
tctgtatgaa cggtctggtc tttgccgacc gcacgccgca tccagcgctg acggaagcaa   1980
aacaccagca gcagttttttc cagttccgtt tatccgggca aaccatcgaa gtgaccagcg   2040
aatacctgtt ccgtcatagc gataacgagc tcctgcactg gatggtggcg ctggatggta   2100
agccgctggc aagcggtgaa gtgcctctgg atgtcgctcc acaaggtaaa cagttgattg   2160
aactgcctga actaccgcag ccggagagcg ccgggcaact ctggctcaca gtacgcgtag   2220
tgcaaccgaa cgcgaccgca tggtcagaag ccgggcacat cagcgcctgg cagcagtggc   2280
gtctggcgga aaacctcagt gtgacgctcc ccgccgcgtc ccacgccatc ccgcatctga   2340
ccaccagcga aatggatttt tgcatcgagc tgggtaataa gcgttggcaa tttaaccgcc   2400
agtcaggctt tctttcacag atgtggattg gcgataaaaa acaactgctg acgccgctgc   2460
gcgatcagtt caccccgtgca ccgctggata cgacattgg cgtaagtgaa gcgacccgca   2520
ttgaccctaa cgcctgggtc gaacgctgga aggcggcggg ccattaccag gccgaagcag   2580
cgttgttgca gtgcacggca gatacacttg ctgatgcggt gctgattacg accgctcacg   2640
cgtggcagca tcagggaaa accttatttta tcagccgaa aacctaccgg attgatggta   2700
gtggtcaaat ggcgattacc gttgatgttg aagtggcgag cgatacaccg catccggcgc   2760
ggattggcct gaactgccag ctggcgcagg tagcagagcg ggtaaactgg ctcggattag   2820
ggccgcaaga aaactatccc gaccgcctta ctgccgcctg ttttgaccgc tgggatctgc   2880
cattgtcaga catgtatacc ccgtacgtct cccgagccga aaacggtctg cgctgcggga   2940
cgcgcgaatt gaattatggc ccacaccagt ggcgcggcga cttccagttc aacatcagcc   3000
gctacagtca acagcaactg atggaaacca gccatcgcca tctgctgcac gcggaagaag   3060
gcacatggct gaatatcgac ggtttccata tggggattgg tggcgacgac tcctggagcc   3120
cgtcagtatc ggcggaattc cagctgagcg ccggtcgcta ccattaccag ttggtctggt   3180
```

```
gtcaaaaata a                                                              3191

<210> SEQ ID NO 4
<211> LENGTH: 65
<212> TYPE: RNA
<213> ORGANISM: Artificial Sequence
<220> FEATURE:
<223> OTHER INFORMATION: Synthetic

<400> SEQUENCE: 4
gggacagauc cacugaggcg uggaucugug aacacuaaac uaaacgacaa uguaaucaaa          60
cuaac                                                                     65
```

METHODS FOR DETECTING TARGET ANALYTES USING SYNTHETIC BIOLOGICAL CIRCUITS THAT MODIFY GLUCOSE LEVELS IN A CELL-FREE SYSTEM

CROSS REFERENCE TO RELATED APPLICATIONS

This application is a national phase entry of PCT/CA2018/051646 filed Dec. 21, 2018 (which designates the U.S.) which claims the benefit of priority of U.S. Provisional Patent Application No. 62/609,525 filed Dec. 22, 2017, the entire contents of which are hereby incorporated by reference.

INCORPORATION OF SEQUENCE LISTING

A computer readable form of the Sequence Listing "2223-P54141US01_SequenceListing.txt" (8,192 bytes), submitted via EFS-WEB and created on Jun. 18, 2020, is herein incorporated by reference.

FIELD OF THE INVENTION

The present invention relates to products and methods for the detection of target analytes and more specifically to products and methods for the detection of target analytes using synthetic biological circuits that produce or consume glucose.

BACKGROUND OF THE INVENTION

The blood glucose monitor is arguably the most widely used diagnostic device and has "revolutionized" the lives of millions of diabetics by enabling the portable quantification, and therefore personal management, of blood sugar. With annual global sales of $11 billion (USD), the glucose meter is an unparalleled success for distributed diagnostics. This widespread adoption has resulted in a global network of device manufacturing, distribution and consumables, as well as broad acceptance by patients and clinicians. This success, however, has not been matched with portable diagnostics for other disease biomarkers (e.g. nucleic acids, proteins and other small molecules). While reasons for this are complex, an important factor is the absence of appropriate portable sensor technology for other classes of analytes.

Previous work to re-purpose personal glucose meters for the detection of analytes other than glucose has been described (Xiang and Lu, 2011; Xiang et al., 2014, Lan et al., 2016). However, the molecular mechanisms used in these reports included the use of aptamers or DNA hybridization between multiple elements and the use of pre-generated enzymes that may limit their utility.

There remains a need for novel products and methods for the detection of target analytes that are readily adapted for use in portable sensor technologies.

SUMMARY OF THE INVENTION

The present invention relates to methods and products useful for detecting a target analyte by activating a synthetic biological circuit in a cell-free system. In one embodiment, activation of the synthetic biological circuit modifies the level of a reporter molecule such as glucose. Detection of the reporter molecule, such as by using a glucose meter, may then be used to detect the presence of the target analyte in a sample.

As shown in FIG. 1, a synthetic biological circuit such as a gene circuit may be used to activate the activity or expression of a reporter enzyme in response to the presence of a target analyte. Various combinations of substrates and enzymes may be selected that result in an increase or decrease in the level of a reporter molecule within the reaction. In a preferred embodiment, the reporter molecule is glucose and the synthetic biological circuit generates and/or activates a reporter enzyme which modifies the level of glucose within the reaction volume. The glucose is generated within the cell-free reaction volume from a substrate that is otherwise inert to a glucose meter, such as a polysaccharide. In one embodiment, glucose is converted into a product (such as D-glucono-1,5-lactone) that is otherwise inert to a glucose meter. Changes in the level of glucose within the reaction volume can readily be determined using a glucose meter and/or glucose test strips. An exemplary assay for detecting a target analyte in a blood sample from a patient using a glucose monitor is shown in FIG. 2.

Furthermore, the embodiments described herein allow for the detection of multiple target analytes within a sample in a single reaction. As shown in FIG. 4, multiple synthetic biological circuits may be used in a cell-free system to generate different levels of glucose in response to different target analytes that are readily distinguished using a glucose monitor.

The embodiments described here present a number of advantages and can be used for detecting target analytes in different sample types for different purposes. For example, the embodiments described herein may be implemented in portable devices suitable for detecting clinically relevant amounts of disease-related DNA/RNA in patient samples. Similarly the technology may be used to genotype individuals at the point-of-care to infer phenotype information, test for the presence of genomic markers in food (e.g. food safety) or analyse environmental samples (e.g. ecological monitoring). Further, by simply changing the upstream gene-based circuit, small molecule analytes such as contaminants (e.g. heavy metals or pesticides), explosives (e.g. national security) or illegal substances (e.g. law enforcement) in a sample of interest may be detected. The methods and products described herein may also be used for detecting molecular barcodes such as those used for tracking items in a supply chain, encrypting information and/or watermarking high value items. The embodiments described herein allow for the use of inexpensive and portable sensors such as a glucose monitor for detecting a wide variety of target analytes.

Accordingly, in one aspect there is provided a method for generating glucose in response to a target analyte in a sample. In one embodiment, the method comprises contacting the sample with a synthetic biological circuit in a cell-free system. The target analyte then activates the synthetic biological circuit to modify a level of glucose within a cell-free system reaction volume.

Optionally, the target analyte activates the synthetic biological circuit to increase the level of glucose within the cell-free system reaction volume or decrease the level of glucose within the cell-free system reaction volume.

In one embodiment, the target analyte is an inorganic molecule or an organic molecule. In one embodiment, the target analyte is a biomolecule such as nucleic acid molecule (DNA or RNA) or a protein.

In one embodiment, the method comprises treating the sample prior to, or during, contact of the sample with the biological circuit in order to purify and/or render available the target analyte(s). For example, in one embodiment the method comprises extracting nucleic acid molecules from the sample. Various methods of nucleic acid extraction known in the art may be used in combination with the embodiments described herein. In one embodiment, the method comprises extracting a target analyte using a substrate such as a paper or membrane that captures the target analyte such as a nucleic acid molecule. In another embodiment, the method comprises the use of magnetic beads for target analyte extraction. In one embodiment, the methods described herein comprise the paper based extraction of nucleic acid molecules from a sample, optionally ReCap RNA extraction as described herein, followed by isothermal nucleic acid sequence-based amplification (e.g. NASBA, RPA, LAMP, etc), prior to contacting the sample with the synthetic biological circuit.

In one embodiment, the method comprises increasing and/or amplifying the concentration of the target analyte in the sample prior to, or during, contact of the sample with the synthetic biological circuit. For example, in one embodiment the method comprises amplifying a target DNA molecule or RNA molecule using nucleic acid amplification techniques known in the art optionally as isothermal amplification techniques.

In one embodiment, the synthetic biological circuit regulates the expression of an enzyme that modifies the level of glucose in the cell-free reaction volume in response to a target analyte, optionally by regulating transcription or translational of the enzyme. In one embodiment, the synthetic biological circuit is a gene circuit. For example, in one embodiment the gene circuit comprises a riboregulator such as a toehold switch that controls the translation of an mRNA encoding the enzyme in response to the target analyte. Alternatively, the synthetic biological circuit may regulate the level or activity of an enzyme that modifies the level of glucose in the cell-free system, optionally by post-translational regulation of the enzyme.

Various combinations of substrates and enzymes may be used in accordance with the embodiments described herein that result in an increase or decrease in the level of a reporter molecule within the cell-free system reaction volume. In one embodiment, the substrate is glucose or a substrate that is acted on by an enzyme to generate glucose. For example, in one embodiment the substrate is trehalose and the enzyme is trehalase. Other combinations of substrates and enzymes will be readily apparent to the skilled person in view of the teachings of the description, including but not limited to, those listed in FIG. 1B. In one embodiment, ketone acetoacetate is generated from HMG-CoA with the enzyme HMG-CoA lyase. In another embodiment, D-3-Hydroxybutyrate is oxidized to acetoacetate using the enzyme 3-hydroxybutyrate dehydrogenase. In one embodiment, β-hydroxybutyrate dehydrogenase is used to converts β-hydroxybutyrate into acetoacetate.

In one embodiment, the methods described herein include treating the sample prior to contacting the sample, or a fraction thereof, with the synthetic biological circuit in the cell-free system. For example, in one embodiment the sample is treated to normalize or lower the concentration of glucose in the sample and/or to increase the relative concentration of the target analyte in the sample. In one embodiment, the sample is treated to remove and/or sequester endogenous glucose and/or blood sugars in the sample. Optionally, the method comprises contacting the sample with glucose dehydrogenase and NAD to convert endogenous glucose to D-glucono-1,5-lactone.

In one embodiment, the methods described herein include detecting the reporter molecule in the cell-free system reaction volume thereby detecting the target analyte in the sample. In one embodiment, the reporter molecule is glucose and a glucose meter and/or glucose test strip is used to detect glucose in the cell-free system reaction volume. In one embodiment, the reporter molecule is a ketone and a ketone meter and/or ketone test strip is used to detect ketones in the cell-free system reaction volume.

The embodiments described herein may also be used to detect a plurality of different target analytes in a multiplex detection reaction. For example, in one embodiment the method comprises contacting the sample with a plurality of synthetic biological circuits in a cell-free system, wherein a different target analyte activates each synthetic biological circuit to modify the level of glucose in the cell-free system reaction volume. In one embodiment, comparing the level of glucose in the cell-free system reaction volume to one or more control levels may be used to determine the presence, absence and/or level of a plurality of target analytes in the sample.

In one embodiment, the methods described herein include presenting data indicative of the presence or absence of one or more target analytes to a user. Optionally, the data is presented to the user on a portable electronic device such as a smart phone.

In another aspect, there is provided a kit comprising a cell-free system comprising a synthetic biological circuit that generates or consumes a reporter molecule in response to a target analyte in a sample. In one embodiment, the reporter molecule is glucose. In one embodiment, the kit comprises a container, optionally a container for receiving the sample and/or contacting the sample with the cell-free system. In one embodiment, the kit comprises reagents for performing a method as described herein. In one embodiment, the kit comprises reagents that operate to form a cell-free system with a synthetic biological circuit. In one embodiment, the cell-free system is freeze dried. In one embodiment, the kit comprises instructions for performing a method for generating a reporter molecule and/or detecting a target analyte as described herein.

In one embodiment, the kit comprises products and/or reagents for processing the sample, such as for extracting nucleic acid molecules from the sample. In one embodiment, the kit comprises a substrate for capturing the target analyte, such as a paper or membrane substrate, optionally cellulose. In one embodiment, the substrate is affixed to a container, optionally to the inside of a container suitable for receiving the sample. In one embodiment, the adherent substrate is affixed to the inside of a removable cap or lid for the container. In one embodiment, the kit comprises magnetic beads suitable for extracting nucleic acids. In one embodiment, the kit comprises reagents for increasing the concentration of the target analyte in the sample. In one embodiment the kit comprises reagents for amplifying a target nucleic acid molecule, optionally for isothermal amplification of the nucleic acid molecule. In one embodiment, the kit comprises a heater for thermal treatment of the sample, optionally for evaporating the sample or lyzing cells in the sample. In one embodiment, thermal treatment prior to contacting the sample with the cell-free system denatures endogenous proteins including glucose-modifying enzymes.

In one embodiment, the kit comprises a container for receiving a sample, wherein the container comprises a removable lid and the substrate is attached to the removable lid. In one embodiment, the kit comprises a plurality of containers and the removable lid is configured to fit the plurality of containers. For example, in one embodiment the kit comprises separate containers for extracting, washing and/or amplifying a target analyte prior to contacting the sample with the synthetic biological circuit. In one embodiment, the kit comprises reagents such as buffers suitable for extracting, washing and/or amplifying the target analyte.

In one embodiment, the kit comprises a synthetic biological circuit comprising a gene circuit. In one embodiment, the gene circuit comprises a riboregulator such as a toehold switch that controls translation of an mRNA encoding an enzyme whose expression generates or consumes glucose in the cell-free system. In one embodiment, the kit comprises a plurality of synthetic biological circuits that generate or consume glucose in response to a plurality of different target analytes in the sample. Optionally, each synthetic biological circuit generates glucose using a different substrate and enzyme.

In one embodiment, the kit further comprises reagents for treating and/or diluting the sample. In one embodiment, the kit comprises reagents to remove and/or sequester endogenous glucose and/or blood sugars in the sample. For example, in one embodiment the kit comprises a predetermined amount of glucose dehydrogenase (GDH) and NAD for converting glucose in the sample to D-glucono-1, 5-lactone.

In one embodiment, the kit further comprises a glucose meter and/or a glucose test strip. In another embodiment, the kit further comprises a ketone meter and/or a ketone test strip.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Embodiments of the invention will now be described in relation to the drawings in which:

FIG. 1B provides a list of reporter enzymes, their respective substrates and the glucose yield per molecule. FIG. 1C shows that an exemplary embodiment of gene circuit-based sensors can function by regulating transcription wherein a TetO-based gene circuit that is repressed by the presence of TetR. This repression is relieved with the addition of the small molecule aTc, which disrupts TetR binding to the TetO promoter, allowing for transcription and translation of a glucose-generating enzyme. FIG. 1D shown a schematic of an exemplary toehold switch-based gene circuit that serves to regulate translation. In the presence of the correct trigger RNA, the 5' RNA hairpin of the toehold switch is linearized, which allows the ribosome to bind to the ribosomal binding site (RBS) and induce translation of the glucose-generating reporter enzyme. FIG. 1E shows the conversion of oligomeric glucose substrates in a cell-free reaction. The oligomeric state of these substrates means that they are non-reactive to the glucose test strips until they have been converted to monomeric glucose by a reporter enzyme output from an activated gene circuit.

DETAILED DESCRIPTION OF THE INVENTION

Figure 1:
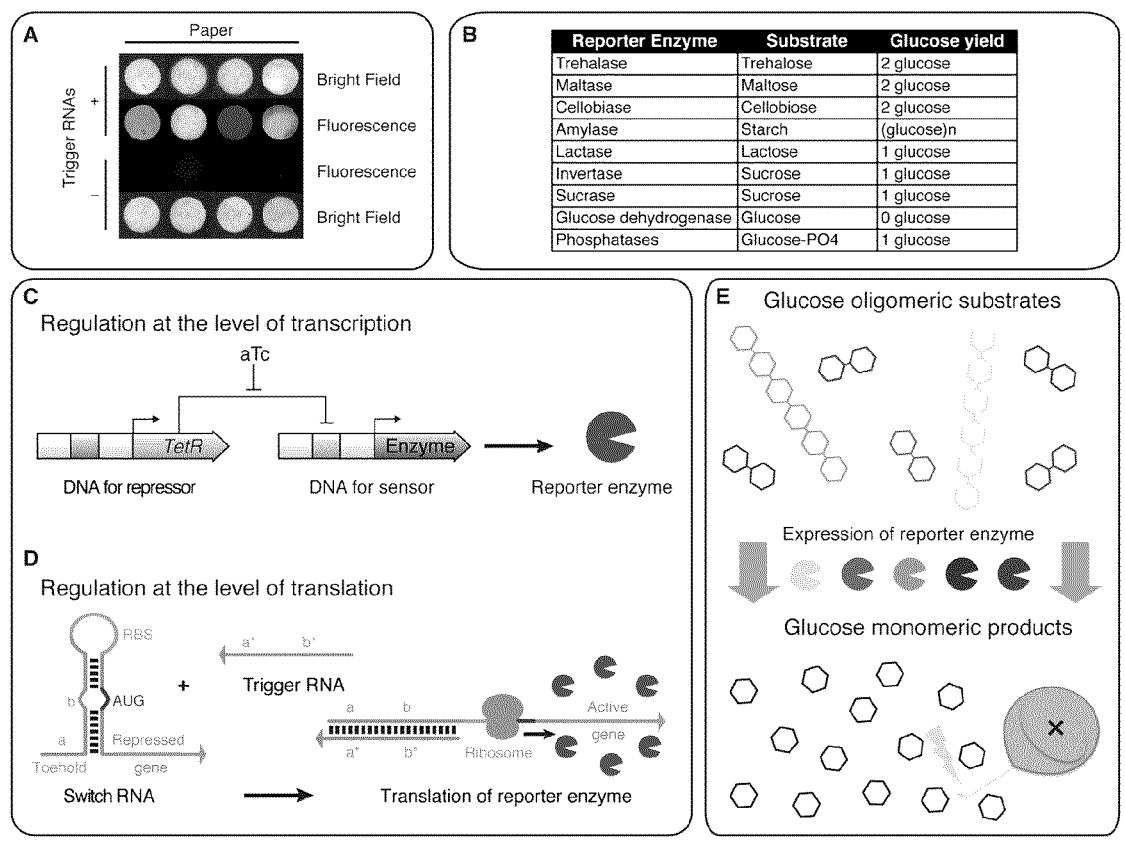
FIG. 1A shows conventional gene circuit-based sensors for detecting target analytes that produce fluorescent or colorimetric protein outputs and require specialized equipment to interpret. Such conventional detection methods are not compatible with widely available diagnostic infrastructures such as glucose meters.
FIGS. 1B, 1C, 1D and 1E show various embodiments for converting a standard glucose meter and test strips into a generic device for the detection of target analytes as described herein using glucose generating enzymes.
Figure 2:
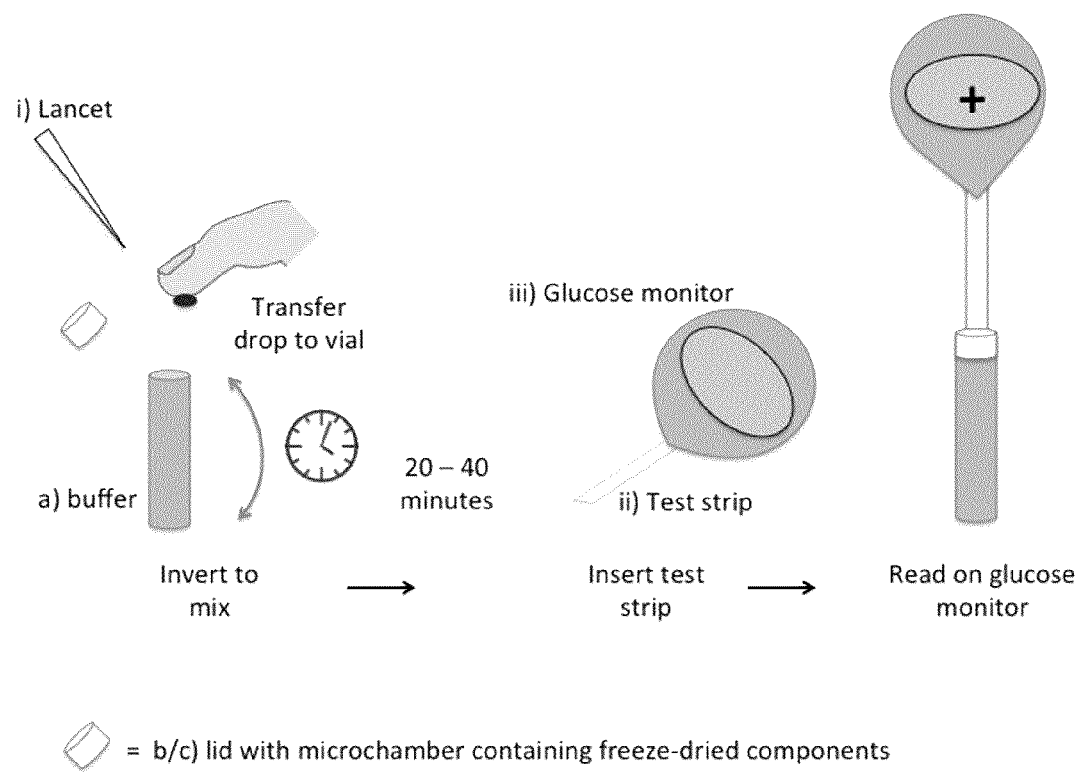
FIG. 2 shows one embodiment of a flow chart for interpreting gene circuit-based RNA sensor output with a glucose meter. A sample may be provided from a subject such as by finger prick using a lancet. The sample is then diluted into a sample preparation buffer vial that includes target specific primers and isothermal amplification reaction mix, and the vial is inverted to mix. After amplification, the amplified target sequence is transferred to a micro-chamber in the lid by removing a seal and inverting the closed vial. The cell-free reaction with RNA sensor is allowed to proceed (optionally for 20-40 minutes) and it is during this period that glucose will be produced if the patient sample is positive for the target analyte. The glucose test strip is then inserted into the micro-chamber and read on the glucose monitor.

The present description provides synthetic biological circuits for the detection of target analytes in a cell-free system. As shown in the Examples, the use of synthetic biological circuits as described allows for the detection of target analytes using readily available sensors and reagents such as glucose monitors and test strips. Different synthetic biological circuits can readily be generated to allow for the detection of different target analytes using the embodiments described herein. For example, target RNA or DNA sequences can be detected using a riboregulator such as a toehold switch to control expression of a reporter enzyme in response to a target nucleic acid sequence. Expression of the reporter enzyme modifies the level of a substrate which is then detected within the cell-free reaction volume. In a preferred embodiment, the reporter enzyme modifies the level of glucose in the cell-free reaction volume enabling the detection of the target analyte using a glucose monitor and/or glucose test strip.

Different reporter enzymes may be used in the same reaction to allow for the simultaneous detection of multiple target analytes. By selecting reporter enzymes that have different rates of modifying the level of a reporter molecule (such as glucose) and preloading different amounts of substrates for each enzyme, the presence or absence of multiple target analytes will result in distinctive levels of the reporter molecule.

As used herein, "cell-free system" refers to a set of reagents capable of providing for or supporting a biosynthetic reaction (e.g., transcription reaction, translation reaction, or both) in vitro in the absence of cells. For example, to provide for a transcription reaction, a cell-free system comprises promoter-containing DNA, RNA polymerase, ribonucleotides, and a buffer system. Cell-free systems can be prepared using enzymes, coenzymes, and other subcellular components either isolated or purified from eukaryotic or prokaryotic cells, including recombinant cells, or prepared as extracts or fractions of such cells. A cell-free system can be derived from a variety of sources, including, but not limited to, eukaryotic and prokaryotic cells, such as bacteria including, but not limited to, *E. coli*, thermophilic or cryophilic bacteria and the like, wheat germ, rabbit reticulocytes, mouse L cells, Ehrlich's ascitic cancer cells, HeLa cells, CHO cells and budding yeast and the like. In one embodiment, the cellular extracts are purified and/or treated to remove endogenous glucose and/or glucose converting enzymes to obtain a cell-free system. Examples of cell-free systems also include the PURExpress® system available from New England Biolabs Inc.

As used herein, the term "biosynthetic reaction" refers to any reaction that results in the synthesis of one or more biological compounds (e.g., DNA, RNA, proteins, monosaccharides, polysaccharides, etc.). For example, a transcription reaction is a biosynthetic reaction because RNA is produced. Other examples of biosynthetic reactions include, but are not limited to, translation reactions, coupled transcription and translation reactions, DNA synthesis, isothermal amplification reactions and polymerase chain reactions.

The term "synthetic biological circuit" used herein refers to any engineered biological circuit where the biological components are designed to perform logical functions. In general, an input is needed to activate a synthetic biological circuit, which subsequently produces an output as a function of the input. In some embodiments, a synthetic biological circuit comprises at least one nucleic acid material or construct. In other embodiments, a synthetic biological circuit is substantially free of nucleic acids. A synthetic gene network is one kind of synthetic biological circuit. Other examples of synthetic biological circuits include, but are not limited to, an engineered signaling pathway, such as a pathway that amplifies input via kinase activity. In one embodiment, the synthetic biological circuit modifies the level of a reporter molecule in a cell-free reaction volume in response to a target analyte. In one embodiment, the synthetic biological circuit regulates the expression and/or activity of an enzyme that generates or consumes a reporter molecule in a cell cell-free reaction volume.

"Synthetic gene network" or "synthetic gene circuit" or "gene circuit" are used interchangeably herein to refer to an engineered composition that comprises at least one nucleic acid material or construct and can perform a function including, but not limited to, sensing, a logic function, and/or a regulatory function. The nucleic acid material or construct can be naturally occurring or synthetic. The nucleic acid material or construct can comprise DNA, RNA, or an artificial nucleic acid analog thereof. In some embodiments of a synthetic gene network comprising at least two nucleic acid materials or constructs, the nucleic acid materials or constructs can interact with each other directly or indirectly. An indirect interaction means that other molecules are required for or intermediate in the interaction. Some examples of synthetic gene networks comprise a nucleic acid operably linked to a promoter. In one embodiment, the gene circuit or gene network comprises a riboregulator such as a toehold switch.

In one aspect there is provided a method for generating a reporter molecule in response to a target analyte in a sample. Preferably, the reporter molecule is a molecule such as glucose that can be detected using a readily available sensor such as a glucose monitor. In one embodiment, the method comprises contacting the sample with a synthetic biological circuit in a cell-free system, wherein the target analyte activates the synthetic biological circuit to modify a level of the reporter molecule within a cell-free system reaction volume.

In one embodiment, the target analyte activates the synthetic biological circuit to increase the level of the reporter molecule within the cell-free system reaction volume. In another embodiment, the target analyte activates the synthetic biological circuit to decrease the level of the reporter molecule within the cell-free system reaction volume. For example, the target analyte may activate the synthetic biological circuit to produce an enzyme that increases the level of glucose by breaking down polymeric sugars.

The methods described herein can be used to detect a variety of different target analytes. In one embodiment, the target analyte is an inorganic molecule such as a metal. In another embodiment, the target analyte is an organic molecule, optionally a biomolecule. Synthetic biological circuits that are activated by various inorganic or organic targets are known in the art and can readily be adapted for use in the methods and kits described herein. For example such circuits are described in Roelof Van der Meer and Belkin (*Nat Rev Microbiol.*, 2010, Jull 8(7)511-522), Zhou et al. *Chem. Rev.*, 2017, 117 (12), pp 8272-8325, and Wedekind et al. (*The Journal of Biological Chemistry* 292, 9441-9450 Jun. 9, 2017), all of which are hereby incorporated by reference.

In one embodiment, the target analyte is a biomolecule such as a nucleic acid (DNA or RNA), protein, lipid, metabolite or sugar molecule. The nucleic acid may be a nucleic acid or variant that is associated with a specific organism and/or phenotype. In one embodiment, the target analyte is a nucleic acid molecule associated with a microbial pathogen, optionally a virus or bacteria. The methods and kits described herein may therefore be used for the detection of specific microbes, optionally for diagnostic purposes. For example, in one embodiment, the target analyte is a nucleic acid molecule associated with microbial drug resistance. In one embodiment, the methods and kits described herein may be used for the detection of enteric fevers such as typhoid or paratyphoid. For example, as shown in Example 4 and FIG. 11, toehold switches configured to activate production of a trehalase enzyme for glucose generation were able to detect RNA targets from typhoid, paratyphoid A or paratyphoid B.

In one embodiment, the sample is from a subject and the target analyte is a biomarker associated with a known phenotype. For example, the biomarker may be associated with a disease or the responsiveness to certain therapies or chemotherapeutic drugs. The methods and products described herein may be used to generate biomarker data for a patient at the point of care, optionally using an inexpensive portable device such as glucose meter.

Figure 17:
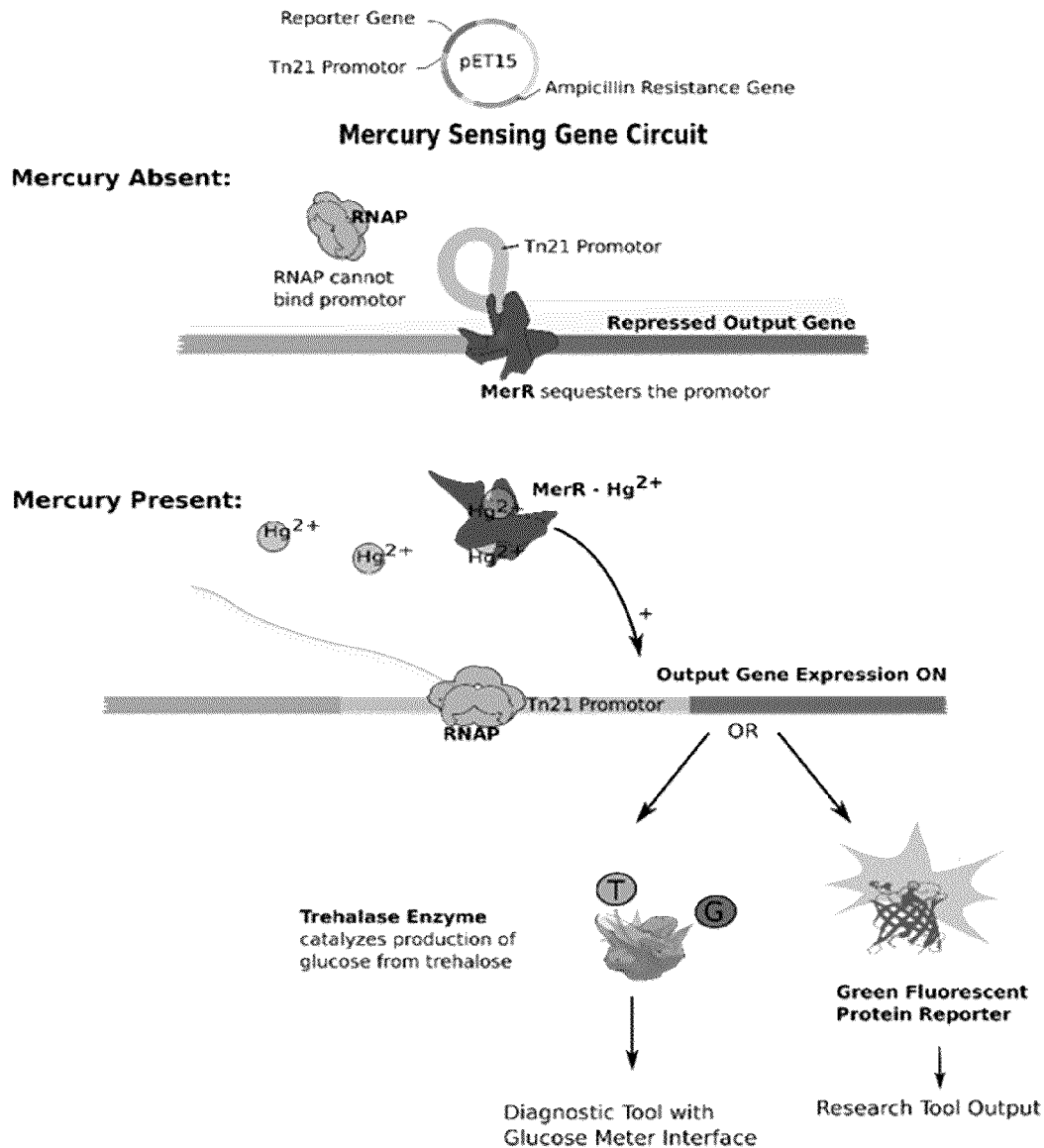
FIG. 17 shows an exemplary glucose meter mediated workflow for the detection of mercury using a synthetic biological circuit.

Alternatively or in addition, the synthetic biological circuits described herein may be used to generate a reporter molecule in response to a metal (e.g. Ni, Co, Fe, Hg), explosive material, herbicide (e.g. atrazine), pollutant and/or toxin. The reporter molecule may then be detected using an inexpensive portable device such as a glucose meter. FIG. 17 shows an exemplary workflow for the detection of mercury using a gene circuit with a Tn21 promoter, which is bound and sequestered by a MerR repressor in the absence of mercury. The Tn21-MerR gene regulatory system is operatively coupled with a trehalase enzyme for the production of glucose, which can then be detected using a glucose meter.

The sample may be subjected to various treatments prior to or during contact with the synthetic biological circuit. In one embodiment, the treatment increases the concentration of the target analyte in the sample. Alternatively, or in addition, the sample may be treated to remove one or more contaminants or to dilute the sample to facilitate detection of the target analyte. In one embodiment, the target analyte is a nucleic acid molecule and the method comprises amplifying the nucleic acid molecule in the sample. For example, in one embodiment, the method comprises isothermal amplification of a target DNA molecule or the target RNA molecule, prior to or during contact with the synthetic biological circuit.

In one embodiment, the methods and kits described herein comprise steps and/or reagents for processing a sample prior to detecting one or more target analytes using the synthetic biological circuit. In one embodiment, nucleic acid molecules are extracted from the sample. Various methods of nucleic acid extraction may be used in combination with the embodiments described herein. As shown in the Examples, an adherent substrate such as cellulose-based paper can be used to capture nucleic acids from a sample, such as a sample of lysed cells. Optionally, the nucleic acid molecules are then retained on the substrate during a washing step, while contaminants present in the sample are removed.

Various techniques known in the art may be used to amplify a nucleic acid molecule within the sample. These include, but are not limited to, polymerase chain reaction (PCR), strand displacement amplification (SDA), loop-mediated amplification (LAMP), Invader assay, rolling circle amplification (RCA), signal mediated amplification of RNA technology (SMART), helicase-dependent amplification (HDA), Nicking Enzyme Amplification Reaction (NEAR), recombinase polymerase amplification (RPA), nicking endonuclease signal amplification (NESA) and nicking endonuclease assisted nanoparticle activation (NENNA), exonuclease-aided target recycling, Junction or Y-probes, split DNAZyme and deoxyribozyme amplification strategies, template-directed chemical reactions that lead to amplified signals, non-covalent DNA catalytic reactions, hybridization chain reactions (HCR) and detection via the self-assembly of DNA probes to give supramolecular structures.

In one aspect of the disclosure, a synthetic biological circuit is constructed to modify the level of a reporter molecule such as glucose in response to the presence of a target analyte. In one embodiment, the synthetic biological circuit regulates the expression, level or activity of an enzyme that modifies the level of the reporter molecule in the cell-free system. Optionally, the synthetic biological circuit may operate by regulating the transcription or translation of the enzyme or by post-translational regulation of the enzyme such as by using small molecule controlled inteins.

In one embodiment, the synthetic biological circuit is a gene circuit. In one embodiment, the gene circuit comprises a DNA molecule comprising a promoter operably linked to a nucleic acid encoding one or more enzymes whose expression modifies the level of a reporter molecule such as glucose in the cell-free system. In one embodiment, the gene circuit regulates the transcription of a DNA molecule encoding one or more enzymes or translation of one or more mRNA molecules encoding one or more enzymes. Optionally, two or more synthetic biological circuits regulate the expression of two or more enzymes that modify the level of glucose. In one embodiment, the two or more enzymes modify the level of glucose at different rates, for example by acting on different substrates.

In one embodiment, the gene circuit comprises one or more transcriptional activators or transcriptional repressors. In one embodiment, the gene circuit comprises a riboregulator that controls translation of an mRNA molecule encoding an enzyme. In one embodiment, the riboregulator is a toehold switch. For example, in one embodiment, the target analyte is a trigger for the toehold switch such that binding of the target analyte to the toehold switch permits translation of the mRNA encoding the enzyme in the gene circuit. A skilled person would readily be able to design toehold switches for various target DNA or RNA molecules.

In one embodiment, the cell-free system comprises one or more substrates that respond to the activity of the biological circuit to modify the level of the reporter molecule. For example, in one embodiment, the cell-free system comprises glucose or a substrate that is acted on by an enzyme under control of the synthetic biological circuit to generate glucose.

In one embodiment, the substrate comprises an oligosaccharide or polysaccharide comprising one or more glucose monomers. Exemplary combinations of enzymes and substrates suitable for use in the synthetic biological circuits described herein are shown in FIG. 1B.

The methods and products described herein may be used to analyze any sample for which information regarding the presence or absence of a target analyte is desired. In one embodiment, the sample is a biological fluid, optionally blood, urine, cerebrospinal fluid or saliva. In one embodiment the sample is a patient sample such as a tissue sample. In another embodiment, the sample is an environmental sample, optionally a water sample. In one embodiment, the sample is a food sample.

In some embodiments, the sample is treated prior to contacting the sample with the synthetic biological circuit in the cell-free system. In one embodiment, treating the sample comprises diluting the sample with a buffer/diluent and/or nuclease free water. In one embodiment, the sample is treated to normalize or lower the concentration of glucose in the sample. The sample may also be treated to remove or reduce the level of contaminants that interfere with the cell-free system and/or the detection of the reporter molecule. In one embodiment, the sample is treated to increase the relative concentration of the target analyte. Alternatively, or in addition, the sample may be subjected to a thermal treatment, such as by heating, cooling and/or freezing the sample. In one embodiment the sample is heated to lyse cells contained in the sample and/or denature endogenous proteins such as naturally occurring enzymes that could interfere with the operation of the cell-free system and/or synthetic biological circuit.

In one embodiment, the sample may be treated to normalize and/or lower the level of a reporter molecule such as glucose in the sample prior to contacting the sample with the synthetic biological circuit. In one embodiment, treating the sample helps control the influence of the sample source, which could potentially include reporter molecules (such as glucose or natural blood sugars) or enzymes that could distort the detection of a target analyte.

In one embodiment, the sample is diluted with a diluent or buffer to reduce the level of the reporter molecule in the sample. In one embodiment, the diluent or buffer comprises a surfactant. In one embodiment, the surfactant is Tween-20. In one embodiment, diluting the sample may bring even high diabetic levels of glucose to below a threshold for the methods described herein. For example, normal glucose levels are 7.8-16.7 mM but occasionally can temporarily exceed 28 mM in extreme hyperglycemia. Diluting the sample by e.g. 10-fold would bring glucose levels to between 0.8 mM and 2.8 mM, which in some embodiments would not be expected to impair the use of the methods described herein.

In some embodiments, the sample may be subjected to additional treatment steps to reduce, remove, sequester and/or normalize the level of glucose. For example, glucose-binding lectins may be used to sequester glucose and/or blood sugars from the sample. In one embodiment, glucose may be removed from the sample by adding an enzyme (e.g. glucose dehydrogenase) that would convert glucose to an inert substance. This process would be limited by the amount of cofactor (e.g. NAD) supplied and tailored to neutralize incoming glucose.

In one embodiment, the method comprises treating the sample with a pre-determined amount of GDH and/or NAD to remove a pre-determined amount of glucose from the sample, such as an average amount of glucose found in a particular sample type.

In one embodiment, the cell-free system comprises a synthetic biological circuit as described herein, enzymes for transcription and translation, ribosomes, dNTPs, tRNAs, and amino acids. Optionally, the cell-free system further comprises one or more of an RNAse inhibitor, a buffer, one or more cofactors, a cryoprotectant and a surfactant, optionally Tween-20. In one embodiment, the cell-free system also comprises a substrate for an enzyme whose expression and/or activity is regulated by the synthetic biological circuit. For example, in one embodiment the cell-free system comprises a pre-determined amount of glucose or a substrate shown in FIG. 1B. In one embodiment, the substrate is a substrate acted on by the enzyme to generate glucose, such as an oligosaccharide or polysaccharide comprising one or more glucose monomers.

The components of the cell-free system may be freeze dried and rehydrated prior to, or as part of a method as described herein. For example, in one embodiment the cell-free system is freeze-dried and rehydrated by contact with the sample, a buffer, and/or diluent.

In one embodiment, the methods described herein include detecting a reporter molecule such as glucose whose level is modified by the synthetic biological circuit. In one embodiment, detection of the presence or absence of the reporter molecule is indicative of the presence or absence of the target analyte in the sample. In one embodiment, the method comprises detecting a level of glucose in the cell-free reaction volume.

In one embodiment, the level of glucose in the cell-free reaction volume is indicative of the level of the target analyte in the sample. In one embodiment, the level of glucose in the cell-free reaction volume is indicative of the presence or absence of a plurality of target molecules detected in a multiplex reaction. In one embodiment, the level of glucose in the cell-free reaction volume is determined at a plurality of time points.

While glucose meters are capable of detecting a wide range of glucose levels, meters have conventionally only been used to generate a single readout (glucose in mg/dL). The methods and kits described herein take advantage of the wide dynamic range of glucose meters to create bandwidth for multiplexed outputs. This can be done by selecting enzymes with different kinetics and controlling substrate concentration. By designing non-overlapping glucose yields for each synthetic biological circuit, multiplexed diagnostics are possible with a single readout number. In one embodiment, each sensor in the multiplexed system produces a unique reporter enzyme that converts an oligomeric glucose substrate into monomeric glucose that can be detected by the glucose meter. By selecting enzymes with different kinetics, and tuning the concentration of substrate, template DNA and other molecular/biochemical parameters, the resulting glucose production can be controlled. In one embodiment, sensor outputs are designed to be non-overlapping so that the additive glucose production can be easily used to determine which sensors were activated.

In one embodiment, the sample is contacted or incubated with the synthetic biological circuit in the cell-free system for a pre-determined amount of time prior to detecting glucose in the cell-free reaction volume. In one embodiment, the sample is contacted or incubated with the synthetic biological circuit in the cell-free system for a period of at least 5, 10, 15, 20, 25, 30, 35, 40 or 45 minutes. In one embodiment, the sample is contacted or incubated with the synthetic biological circuit in the cell-free system for a period of 30-180 minutes, optionally between 30 and 90 minutes or between 60 and 90 minutes.

In one embodiment, the method comprises adding a buffer to the cell-free system reaction volume prior to detecting glucose. In one embodiment, the buffer is a composition comprising 0.1 M NaCl, 0.1 M sodium phosphate, 0.05% Tween-20 and has a pH of about 7.3. IN one embodiment, the buffer comprises or consists of Tween-20, optionally about 0.0125% Tween-20 or between 0.01% and 0.02% Tween-20.

In one embodiment, the methods described herein include detecting a level of glucose using a glucose meter, optionally using a glucose test strip. In one embodiment, the method comprises contacting the cell-free reaction volume, or a portion thereof, with a glucose test strip.

As shown in Example 3, the use of a more than one synthetic biological circuit as described herein can be used to detect a plurality of target analytes in a single reaction volume. In one embodiment, the method comprises contacting the sample with a plurality of synthetic biological circuits in a cell-free system, wherein a different target analyte activates each synthetic biological circuit to modify a level of a reporter molecule in the cell-free reaction volume. In one embodiment, each of the plurality of synthetic biological circuits generates glucose using a different substrate and enzyme. In one embodiment, differences in the rate and/or level of the reporter molecule generated by the plurality of synthetic biological circuits in the cell-free system allows for the multiplex detection of a plurality of different target analytes in a single reaction.

Figure 10:
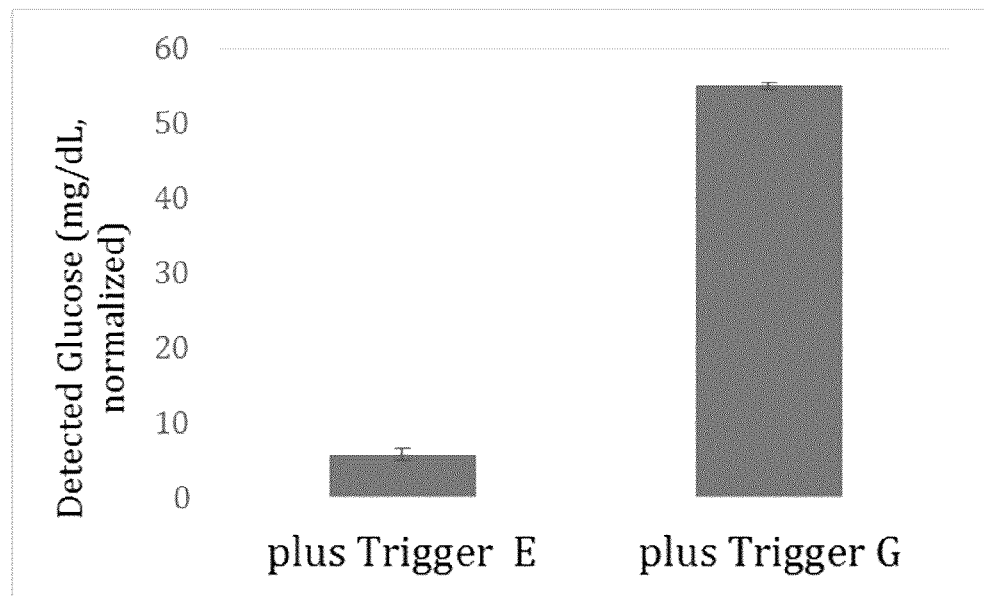
FIG. 10A shows multiplexing using two different toehold switches for different target analytes in a single reaction volume.
FIG. 10B shows results from a similar experiment for and the multiplexed detection of two different target RNA sequences using two different glucose-generating enzymes.
FIG. 10C shows multiplexed detection using the same enzyme where reporter activity has been tuned using different toehold switches (toehold switches can have variable levels of activity) and different amounts of DNA encoding each of the toehold switches (ie: the amount of sensor present).
Figure 10:
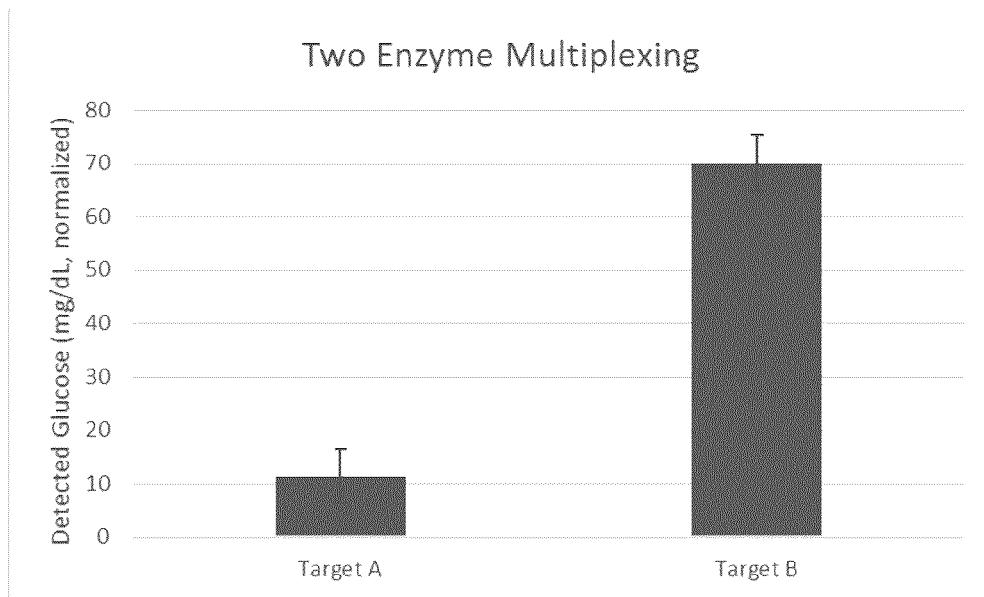
Figure 10:
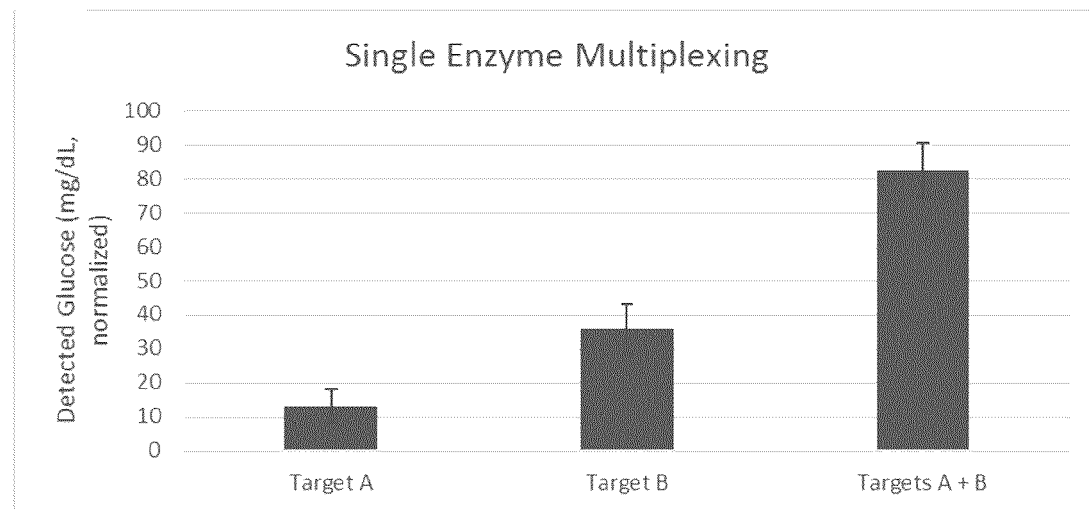

As shown in FIGS. 10A and 10B, the methods and kits described herein are useful for multiplexing using two separate enzymes that, for example, produce glucose at different rates, or, as in FIG. 10C, with a single enzyme wherein each target activates the production of a single enzyme, but at different rates.

Optionally, the methods described herein include comparing the level of glucose detected in the cell-free system reaction volume to one or more control levels. In one embodiment, the control level is indicative of a pre-determined level of the target analyte in a control sample tested under similar conditions. In one embodiment, the method comprises comparing the level of glucose detected in the cell-free system reaction volume to one or more control levels, wherein each control level is indicative of the presence or absence of one or more the target analytes in the sample.

In one embodiment, the methods described herein comprise presenting data indicative of the presence or absence of one or more target analytes in the sample to a user. For example, the data may be indicative of the level of the one or more target analytes in the sample. In one embodiment, the data may be indicative of a phenotype or other condition associated with the presence of a target analyte in the sample.

In another aspect of the description, there is provided a kit comprising a cell-free system comprising a synthetic biological circuit that generates or consumes a reporter molecule in response to a target analyte in a sample. In one embodiment, the reporter molecule is glucose. In another embodiment, the reporter molecule is a ketone. In one embodiment, the kit comprises reagents, such as, but not limited to, those in the cell-free system or reagents for increasing the concentration of a target analyte. In one embodiment, the kit comprises reagents for performing a method as described herein.

In one embodiment, the kit comprises a container for receiving the sample and contacting the sample with the cell-free system. In one embodiment, the container comprises a lid and a receptacle. Optionally, the container is adapted to receive a glucose test strip such that a cell-free reaction volume within the container is in contact with the glucose test strip. In one embodiment, the container comprises a chamber containing the cell-free system. For example, in one embodiment the chamber is located in the lid. Optionally, the cell-free system may be freeze dried and positioned within the container. In one embodiment, the cell-free system is associated with a substrate, such as a paper or another inert material.

In one embodiment, the kit comprises a plurality of containers useful in a workflow as described herein. For example, in one embodiment the kit comprises a first container suitable for receiving a sample and extracting nucleic acids onto an adherent substrate. In one embodiment, the kit comprises a second container suitable for washing the adherent substrate to remove impurities. In one embodiment, the kit comprises a third container suitable for eluting nucleic acid molecules captured on the substrate, and optionally for amplifying the nucleic acid molecules in the sample prior to contacting the sample with the synthetic biological circuit. In one embodiment, the adherent substrate is affixed to a lid or cap that is configured to fit one or more of the three containers. This facilitates the transfer of the sample containing the target analyte between the different containers for processing and/or amplifying the sample prior to contact with the synthetic biological circuit.

In one embodiment, the kit comprises reagents for extracting and/or washing a target analyte from a sample. In one embodiment, the kit comprises an extraction buffer suitable for lysing cells to extract nucleic acids. In one embodiment, the kit comprises a wash buffer suitable for removing impurities from a sample of nucleic acid molecules.

In one embodiment, the target analyte is a nucleic acid molecule and the kit comprises reagents for increasing the concentration of the nucleic acid molecule. In one embodiment, the kit comprises reagents for the isothermal amplification of the nucleic acid molecule. Optionally, the reagents for increasing the concentration of the target analyte are combined with the cell-free system within the container or are provided separately within or outside of the container.

In one embodiment, the synthetic biological circuit is a gene circuit. For example, in one embodiment the gene circuit comprises a DNA molecule comprising a promoter operably linked to a nucleic acid encoding one or more enzymes whose expression generates or consumes the reporter molecule in the cell-free system. In one embodiment, the gene circuit comprises a riboregulator that controls translation of an mRNA encoding an enzyme whose expression generates or consumes the reporter molecule in the cell-free system. In one embodiment, the riboregulator is a toehold switch. In one embodiment, the reporter molecule is glucose.

In one embodiment, the cell-free system in the kit comprises glucose or a substrate that is acted on by the enzyme to generate glucose. For example, in one embodiment the cell-free system comprises a pre-determined amount of glucose or a substrate shown in FIG. 1B. In one embodiment, the substrate is acted on by the enzyme to generate glucose, such as an oligosaccharide or polysaccharide comprising one or more glucose monomers.

In one embodiment, the kit comprises reagents for treating the sample prior to contacting the sample with the cell-free system. In one embodiment, the kit comprises reagents for treating the sample to remove and/or sequester endogenous glucose and/or blood sugars from the sample. For example, in one embodiment the kit comprises glucose dehydrogenase (GDH) and NAD, optionally a pre-determined amount of GDH and/or NAD. In one embodiment, the kit comprises lectins to sequester glucose and/or blood sugars in the sample. In one embodiment, the reagents for treating the sample to remove and/or sequester endogenous glucose and/or blood sugars are provided in the kit separated from the cell-free system.

In one embodiment, the kit comprises a diluent or buffer. In one embodiment, the diluent or buffer may be used to dilute the sample and/or rehydrate a cell-free system. In one embodiment, the diluent or buffer comprises nuclease free water and/or a surfactant, optionally Tween-20. In one embodiment, the diluent or buffer is provided within the container separated from the cell-free system. In use, the sample and the diluent or buffer may be contacted with the cell-free system to activate the synthetic biological circuit in response to a target molecule.

In one embodiment, the cell-free system comprises a synthetic biological circuit as described herein, enzymes for transcription and translation, ribosomes, dNTPs, tRNAs, and amino acids. Optionally, the cell-free system further comprises an RNAse inhibitor, a buffer, one or more cofactors, a cryoprotectant and/or a surfactant, optionally Tween-20. In one embodiment, the cell-free system comprises a substrate for an enzyme whose expression and/or activity is regulated by the synthetic biological circuit such as a substrate shown in FIG. 1B.

In one embodiment, the kit comprises a plurality of different synthetic biological circuits that are activated by different target analytes. For example, different kits may be provided, either alone or in combination, for the detection of different target analytes or combinations of target analytes.

In one embodiment, the kit comprises a device and/or reagents suitable for detecting the reporter molecule within the cell-free reaction volume. For example, in one embodiment the kit comprises a glucose meter and optionally one or more glucose test strips.

Example 1

Use of Synthetic Biological Circuits for Producing Glucose in Response to a Target Analyte in a Cell-Free System A series of experiments were performed to demonstrate the use of synthetic biological circuits to generate glucose in response to a target analyte in a cell-free reaction. For all experiments, glucose was detecting using a commercially available blood glucose meter and associated test strips (Bayer Contour Blood Glucose Monitoring System).

Figure 3:
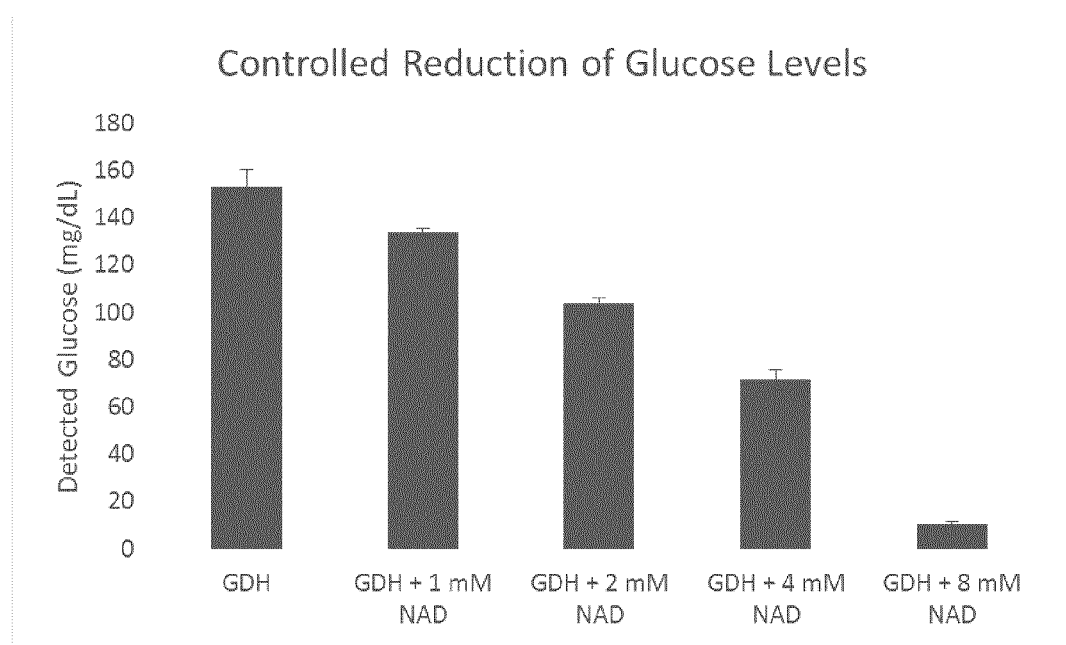
FIG. 3 shows the controlled reduction of glucose by titrating the NAD co-substrate for glucose dehydrogenase (GDH). When GDH is expressed in cell-free reactions, the amount of glucose catabolized by the enzyme can be controlled with precision by supplying the different amounts NAD. NAD is reduced by GDH to NADH and is required for the catabolism of glucose at a 1:1 ratio. GDH may be used as a diagnostic reporter enzyme or to reduce endogenous glucose present in a sample prior to running the assay.

Endogenous levels of glucose within a sample could potentially interfere with the use of glucose as a reporter molecule, especially for the analysis of biological samples. As shown in FIG. 3, it is possible to effect a controlled reduction of glucose within a sample using glucose dehydrogenase (GDH) and titrating in the cofactor NAD. GDH and NAD may therefore be used to treat a sample to reduce or normalize the level of glucose prior to analysis using the cell-free system.

Next, experiments were performed using the PUREx-press® cell-free system commercially available from New England Biolabs (NEB) that includes reconstituted purified components necessary for transcription/translation from *E. coli*. A recombinant construct "Toehold Switch G" was generated with a T7 promoter (in italics) and toehold switch G(underlined) operably connected to DNA encoding trehalase enzyme (SEQ ID NO: 1):

```
                                                                       (SEQ ID NO: 1)
TAATACGACTCACTATAGGGATCTATTACTACTTACCATTGTCTTGCTCTATACAGAAACAGAGGAGAT

ATAGAATGAGACAATGGAACCTGGCGGCAGCGCAAAAGATGCGTAAAGATTATAAAGATGATGATGATA

AAGGACATCATCATCATCATCACAGCAGCGGCGAGAACCTGTACTTCCAATCCTCTGGAGGTGGGGGTT

CTGGAACAGCGGTACGGATAGATTATGCAAGCGGGTTAACTGATCGCGAAAACTCTATGTTCAAAGAAA

TCCAGTTGTCAGGCGTTTTTGCCGATTCAAAAACCTTTGTGGATAGCCATCCCAAATTGCCCCTGGCGG
```

-continued

```
AAATCGCCGAGCTTTACCATGTCCGGCAACAGCAGGCGGGTTTTGACCTCGCCGCTTTTGTTCACCGGT

ATTTTGAGCTGCCGCCGAGCATTGCCTCCGGTTTTGTCAGCGATACCTCGCGCCCGGTGGAAAAGCATA

TCGACATTCTCTGGGATGTGCTCACCCGCCAACCGGACAGGCAGGAGGCGGGAACCCTGCTGCCCTTAC

CTTACCCCTATGTCGTTCCCGGCGGCCGCTTCCGCGAAATTTACTACTGGGACAGCTATTTCACCATGC

TCGGTTTGCAGGCATCGAAGCGCTGGGATCTGATGGAGGGTATGGTGAATAATTTTTCACACCTGATCG

ACACCATCGGCTTTATTCCCAACGGCAATCGCACCTATTACGAGGGCCGCTCCCAGCCGCCTTTTTACG

CCCTGATGGTGGAGTTGCTGGCCAATAAACAGGGTGAGTCGGTGCTGCTCGCGCATTTGCCGCATTTGC

GCAGGGAATATGAATTCTGGATGGAGGGCGCCGCTAAACTTTCGCCCGCTGCACCCGCGCATCGCCGTG

TGGTGCTGCTGCCGGATGGCAGCATACTCAATCGCTACTGGGATGATATAGCCGCGCCGCGCCCGGAAT

CCTTCCGCGAAGACTACGAACTGGCGGAAGCCATCGGCGGCAACAAGCGCGAGCTGTACCGCCATATTC

GCGCGGCGGCAGAATCCGGCTGGGACTTCAGCAGCCGCTGGTTCAAAGATGGCAATGGCATGGCCAGCA

TCCACACCACCGATATTATCCCGGTGGATTTGAATGCGCTGGTCTTTAACCTGGAGCGGATGCTGGCCC

ATATTTATGGCTTGCAGGGCGACCAGGATCAGGCCACGCATTACTACCAATTGGCGGAGCAGCGCAAAC

AGGCGTTGCTGCGCTACTGTTGGAATGCGCAGCAGGGATTTTTCCACGATTACGATTATGTCGCCGCAC

AACAGACGCCGGTCATGTCGCTGGCGGCGGTTTACCCGCTTTATTTCAGTATGGTCGACCAGCGCACGG

GCGACCGGGTCGCCGAACAGATAGAGGCGCATTTTATCCAGGCGGGCGGTGTGACCACGACCCTGGCGA

CCACAGGCCAGCAGTGGGACGCGCCCAATGGCTGGGCGCCGCTGCAATGGCTGACCATCCAGGGCCTGC

GCAATTATCACCACAATTCAGCGGCGGAGCAGATCAAACAGCGCTGGATTGCACTCAACCAGCGCGTTT

ACCGCAACACCGGAAAGTTGGTGGAAAAATACAACGTCTATGACCTGGATGTGGCCGGCGGCGGTGGCG

AATATGAATTACAGGATGGCTTCGGTTGGACCAACGGTGTCTTGTTGCACTTACTCAACGAAAGTACAC

CCTAA
```
35

Toehold switch G is activated by RNA trigger sequence G below (SEQ ID NO: 2):

```
                                            (SEQ ID NO: 2)
GGGUGAUGGGACAUUCCGAUGUCCCAUCAAUAAGAGCAAGACAAUGGUAA

GUAGUAAUAGAUAAG
```
40

Figure 4:
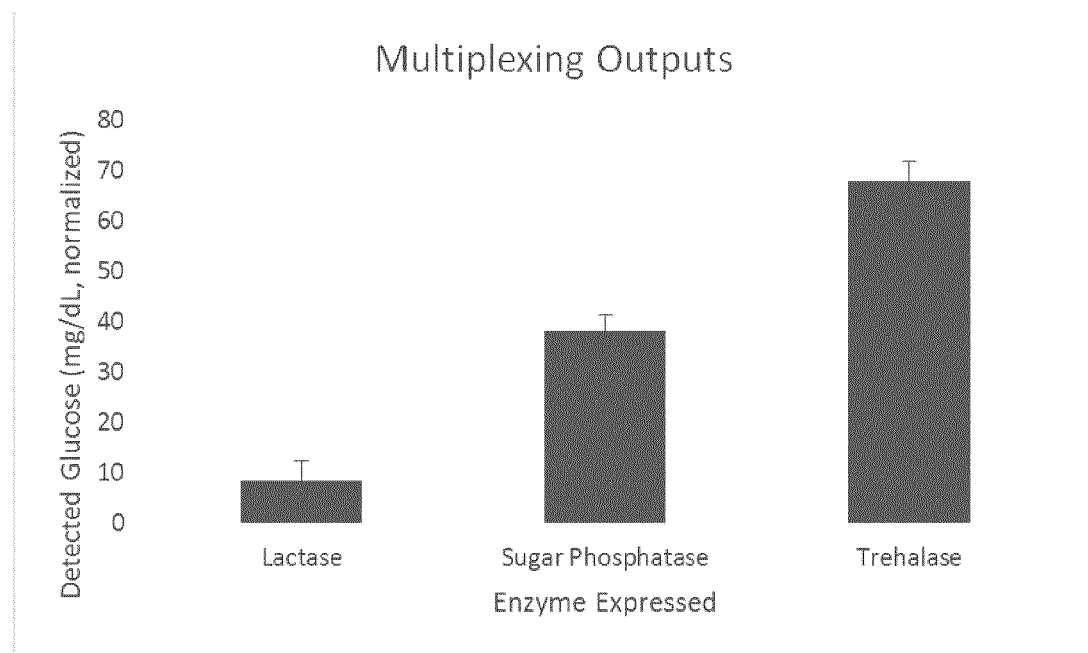
FIG. 4 shows the use of signal intensity for multiplexed outputs from diagnostic cell-free reactions. Adding DNA templates for different enzymes into a common reaction mix allows for the reaction to generate different levels of glucose in response to different target analytes. This can be used to operate multiple diagnostic sensors in a single reaction. All reactions were performed using a cell-free expression system, and are identical except for the DNA added as described in Example 1. Enzymes were expressed in the system from plasmid DNA. Lactase expression was under control of a toehold switch, with trigger added. The other two enzymes were expressed from a standard T7 promotor. All values are shown after subtraction of background signal, determined by measuring a control reaction without any DNA added. Cell-free reactions were incubated at 37° C. for 1 hour. Glucose concentration was measured using a blood glucose meter.
Figure 5:
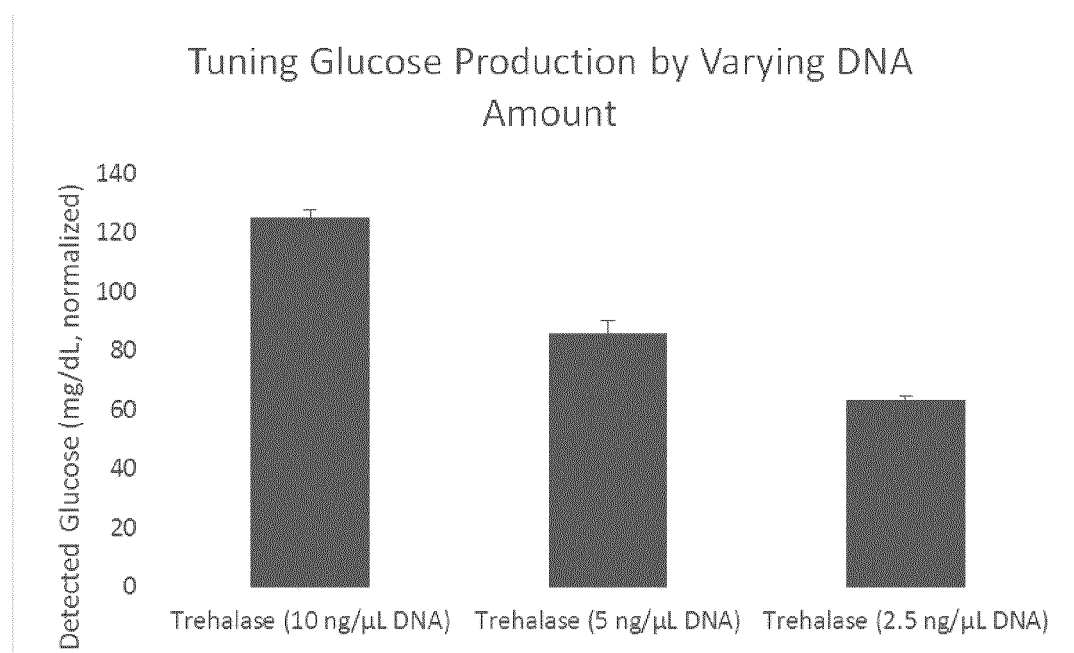
FIG. 5 shows that titrating the amount of DNA template for an enzyme can control the amount of glucose generated by a reaction. A reduction in the amount of template DNA results in slower glucose production. This may be used in diagnostic systems to tune the output from different enzymes to create clear differences between signal intensities for multiplexing. Values are shown after subtraction of background signal, determined using a negative control reaction with no DNA present. Samples were incubated at 37° C. for 1 hour. Glucose concentration was measured using a blood glucose meter.
Figure 6:
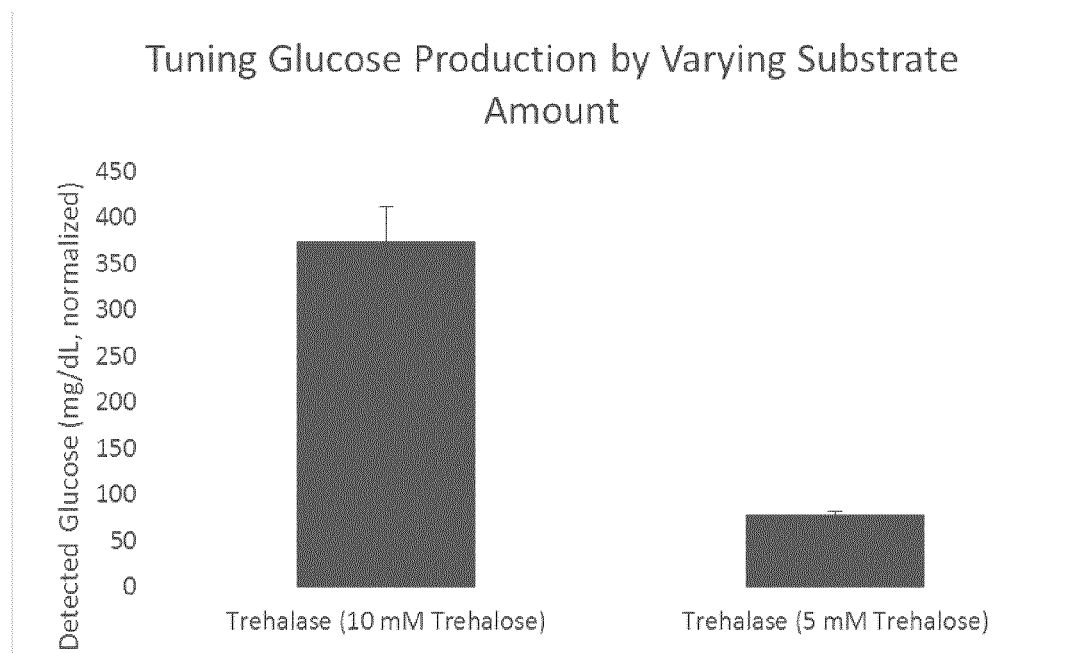
FIG. 6 shows the effect of substrate concentration on glucose production. Different levels of trehalose substrate result in different concentrations of glucose in the presence of trehalase. Values are shown after subtraction of background signal, determined using a negative control reaction with no DNA present. Cell-free reactions were incubated at 37° C. for 1 hour. Glucose concentration was measured using a blood glucose meter.
Figure 7:
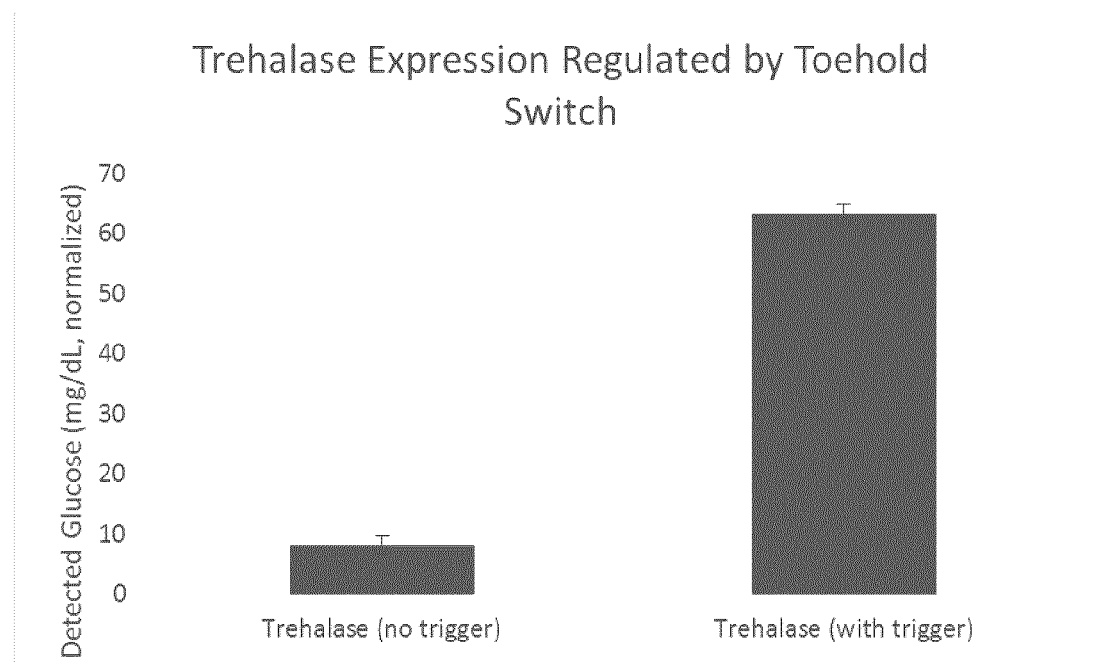
FIG. 7 shows the expression of trehalase under the control of a toehold switch-based RNA sensor. This represents a simulated diagnostic reaction where the presence of trigger RNA induces the translation of trehalase and the concomitant production of glucose. Trehalase converts each molecule of trehalose into two glucose molecules. Values are shown after subtraction of background signal, determined using a negative control reaction with no DNA present. Cell-free reactions were incubated at 37° C. for 1 hour. Glucose concentration was measured using a blood glucose meter.

As shown in FIGS. 4-6, by using different reporter enzymes as outputs from synthetic biological circuits, different concentrations of glucose can be generated. This feature can be used to differentiate between the activity of different synthetic biological circuits (sensing different analytes) in a single reaction volume and glucose measurement (FIG. 4). Similarly, the concentration of DNA template and enzyme substrate can be controlled to tune the glucose yield from a reporter enzyme (FIGS. 5 and 6). Furthermore, as shown in FIG. 7 a simulated diagnostic using a cell-free system and toehold switch G resulted in the production of glucose in response to the target analyte (RNA trigger sequence G) that was readily detected using a portable blood glucose meter.

Example 2

Use of a Toehold Switch to Regulate Lactase Expression in a Cell-Free System

A series of cell-free reactions were assembled following a reaction template using a toehold switch to control lactase expression as shown in Table 1.

TABLE 1

Assembly of master mix and individual reactions for cell-free systems with lactase (also known as beta-galactosidase or LacZ) under the control of a toehold switch. Volumes in microliters.

Master Mix Assembly

| Treatment | | NEB A (0.4) | NEB B (0.3) | (0.005) Stock Conc. | Lactose (mM) | Tween-20 (1%) |
|---|---|---|---|---|---|---|
| | | 2.50 | 3.33 | 200.00 Final Conc. | 1460.00 | 1.00 |
| | | 40% of total volume | 30% of total volume | | 20 mM | 0.0125 |
| Neg control - cell-free alone | NEB | 3.20 | 2.40 | 0.04 | 0.11 | 0.10 |
| Positive control - glucose spike | Glucose | 3.20 | 2.40 | 0.04 | 0.11 | 0.10 |
| Toehold switch alone | LacZSwE | 3.20 | 2.40 | 0.04 | 0.11 | 0.10 |
| Toehold switch + Trigger RNA | LacZSwE + Trig | 3.20 | 2.40 | 0.04 | 0.11 | 0.10 |
| | Master Mix | 14.1 | 10.6 | 0.18 | 0.48 | 0.44 |

Assembly of Individual Reactions.

| Treatment | Master mix | Glucose (mM) 200.00 10 mM | LacZ Switch 97.00 10 ng/uL | LacZ Trigger 257.00 15 ng/uL | ddH2O | Total Volume |
|---|---|---|---|---|---|---|
| Neg control - cell-free alone | 5.85 | 0.00 | 0.00 | 0.00 | 2.15 | 8.00 |
| Positive control - glucose spike | 5.85 | 0.40 | 0.00 | 0.00 | 1.75 | 8.00 |
| Toehold switch alone | 5.85 | 0.00 | 0.82 | 0.00 | 1.33 | 8.00 |
| Toehold switch + Trigger RNA | 5.85 | 0.00 | 0.82 | 0.62 | 0.70 | 8.00 |
| Totals | 23.40 | 0.40 | 1.65 | 0.62 | 5.93 | 32.00 |

Toehold switch with beta-galactosides (LacZ) reporter enzyme
* Enzyme substrate lactose
* Reaction volumes in uL

35

A recombinant construct "Toehold Switch E" was generated with a T7 promoter (in italics) and toehold switch E (underlined) operably connected to DNA encoding a lactase reporter enzyme (SEQ ID NO: 3):

```
                                                    (SEQ ID NO: 3)
TAATACGACTCACTATAGGGAGTTTGATTACATTGTCGTTTAGTTTAGTGATACATAAACAGAGGAGAT

ATCACATGACTAAACGAAACCTGGCGGCAGCGCAAAAGATGCGTAAAATGACCATGATTACGGATTCAC

TGGCCGTCGTTTTACAACGTCGTGACTGGGAAAACCCTGGCGTTACCCAACTTAATCGCCTTGCAGCAC

ATCCCCCTTTCGCCAGCTGGCGTAATAGCGAAGAGGCCCGCACCGATCGCCCTTCCCAACAGTTGCGCA

GCCTGAATGGCGAATGGCGCTTTGCCTGGTTTCCGGCACCAGAAGCGGTGCCGGAAAGCTGGCTGGAGT

GCGATCTTCCTGAGGCCGATACTGTCGTCGTCCCCTCAAACTGGCAGATGCACGGTTACGATGCGCCCA

TCTACACCAACGTGACCTATCCCATTACGGTCAATCCGCCGTTTGTTCCCACGGAGAATCCGACGGGTT

GTTACTCGCTCACATTTAATGTTGATGAAAGCTGGCTACAGGAAGGCCAGACGCGAATTATTTTTGATG

GCGTTAACTCGGCGTTTCATCTGTGGTGCAACGGGCGCTGGGTCGGTTACGGCCAGGACAGTCGTTTGC

CGTCTGAATTTGACCTGAGCGCATTTTTACGCGCCGGAGAAAACCGCCTCGCGGTGATGGTGCTGCGCT

GGAGTGACGGCAGTTATCTGGAAGATCAGGATATGTGGCGGATGAGCGGCATTTTCCGTGACGTCTCGT

TGCTGCATAAACCGACTACACAAATCAGCGATTTCCATGTTGCCACTCGCTTTAATGATGATTTCAGCC

GCGCTGTACTGGAGGCTGAAGTTCAGATGTGCGGCGAGTTGCGTGACTACCTACGGGTAACAGTTTCTT

TATGGCAGGGTGAAACGCAGGTCGCCAGCGGCACCGCGCCTTTCGGCGGTGAAATTATCGATGAGCGTG

GTGGTTATGCCGATCGCGTCACACTACGTCTGAACGTCGAAAACCCGAAACTGTGGAGCGCCGAAATCC

CGAATCTCTATCGTGCGGTGGTTGAACTGCACACCGCCGACGGCACGCTGATTGAAGCAGAAGCCTGCG
```

-continued
```
ATGTCGGTTTCCGCGAGGTGCGGATTGAAAATGGTCTGCTGCTGCTGAACGGCAAGCCGTTGCTGATTC

GAGGCGTTAACCGTCACGAGCATCATCCTCTGCATGGTCAGGTCATGGATGAGCAGACGATGGTGCAGG

ATATCCTGCTGATGAAGCAGAACAACTTTAACGCCGTGCGCTGTTCGCATTATCCGAACCATCCGCTGT

GGTACACGCTGTGCGACCGCTACGGCCTGTATGTGGTGGATGAAGCCAATATTGAAACCCACGGCATGG

TGCCAATGAATCGTCTGACCGATGATCCGCGCTGGCTACCGGCGATGAGCGAACGCGTAACGCGAATGG

TGCAGCGCGATCGTAATCACCCGAGTGTGATCATCTGGTCGCTGGGGAATGAATCAGGCCACGGCGCTA

ATCACGACGCGCTGTATCGCTGGATCAAATCTGTCGATCCTTCCCGCCCGGTGCAGTATGAAGGCGGCG

GAGCCGACACCACGGCCACCGATATTATTTGCCCGATGTACGCGCGCGTGGATGAAGACCAGCCCTTCC

CGGCTGTGCCGAAATGGTCCATCAAAAAATGGCTTTCGCTACCTGGAGAGACGCGCCCGCTGATCCTTT

GCGAATACGCCCACGCGATGGGTAACAGTCTTGGCGGTTTCGCTAAATACTGGCAGGCGTTTCGTCAGT

ATCCCCGTTTACAGGGCGGCTTCGTCTGGGACTGGGTGGATCAGTCGCTGATTAAATATGATGAAAACG

GCAACCCGTGGTCGGCTTACGGCGGTGATTTTGGCGATACGCCGAACGATCGCCAGTTCTGTATGAACG

GTCTGGTCTTTGCCGACCGCACGCCGCATCCAGCGCTGACGGAAGCAAAACACCAGCAGCAGTTTTTCC

AGTTCCGTTTATCCGGGCAAACCATCGAAGTGACCAGCGAATACCTGTTCCGTCATAGCGATAACGAGC

TCCTGCACTGGATGGTGGCGCTGGATGGTAAGCCGCTGGCAAGCGGTGAAGTGCCTCTGGATGTCGCTC

CACAAGGTAAACAGTTGATTGAACTGCCTGAACTACCGCAGCCGGAGAGCGCCGGGCAACTCTGGCTCA

CAGTACGCGTAGTGCAACCGAACGCGACCGCATGGTCAGAAGCCGGGCACATCAGCGCCTGGCAGCAGT

GGCGTCTGGCGGAAAACCTCAGTGTGACGCTCCCCGCCGCGTCCCACGCCATCCCGCATCTGACCACCA

GCGAAATGGATTTTTGCATCGAGCTGGGTAATAAGCGTTGGCAATTTAACCGCCAGTCAGGCTTTCTTT

CACAGATGTGGATTGGCGATAAAAAACAACTGCTGACGCCGCTGCGCGATCAGTTCACCCGTGCACCGC

TGGATAACGACATTGGCGTAAGTGAAGCGACCCGCATTGACCCTAACGCCTGGGTCGAACGCTGGAAGG

CGGCGGGCCATTACCAGGCCGAAGCAGCGTTGTTGCAGTGCACGGCAGATACACTTGCTGATGCGGTGC

TGATTACGACCGCTCACGCGTGGCAGCATCAGGGGAAAACCTTATTTATCAGCCGGAAAACCTACCGGA

TTGATGGTAGTGGTCAAATGGCGATTACCGTTGATGTTGAAGTGGCGAGCGATACACCGCATCCGGCGC

GGATTGGCCTGAACTGCCAGCTGGCGCAGGTAGCAGAGCGGGTAAACTGGCTCGGATTAGGGCCGCAAG

AAAACTATCCCGACCGCCTTACTGCCGCCTGTTTTGACCGCTGGGATCTGCCATTGTCAGACATGTATA

CCCCGTACGTCTTCCCGAGCGAAAACGGTCTGCGCTGCGGGACGCGCGAATTGAATTATGGCCCACACC

AGTGGCGCGGCGACTTCCAGTTCAACATCAGCCGCTACAGTCAACAGCAACTGATGGAAACCAGCCATC

GCCATCTGCTGCACGCGGAAGAAGGCACATGGCTGAATATCGACGGTTTCCATATGGGGATTGGTGGCG

ACGACTCCTGGAGCCCGTCAGTATCGGCGGAATTCCAGCTGAGCGCCGGTCGCTACCATTACCAGTTGG

TCTGGTGTCAAAAATAA
```

Toehold switch E is activated by RNA trigger sequence E below (SEQ ID NO: 4):

(SEQ ID NO: 4)
GGGACAGAUCCACUGAGGCGUGGAUCUGUGAACACUAAACUAAACGACAA

UGUAAUCAAACUAAC

Figure 8:
FIG. 8 shows the expression of lactase under the control of a toehold switch-based RNA sensor. Here the translation of the reporter enzyme lactase is induced in the presence of the correct RNA trigger sequence, resulting in the production of glucose. Lactase converts each molecule of the sugar lactose into one glucose molecule (plus one galactose). Here, leakage is undetectable, likely due to the slower reaction speed of this enzyme. Values are shown after subtraction of background signal, determined using a negative control reaction with no DNA present. Cell-free reactions were incubated at 37° C. for 1 hour. Glucose concentration was measured using a blood glucose meter.
Figure 9:
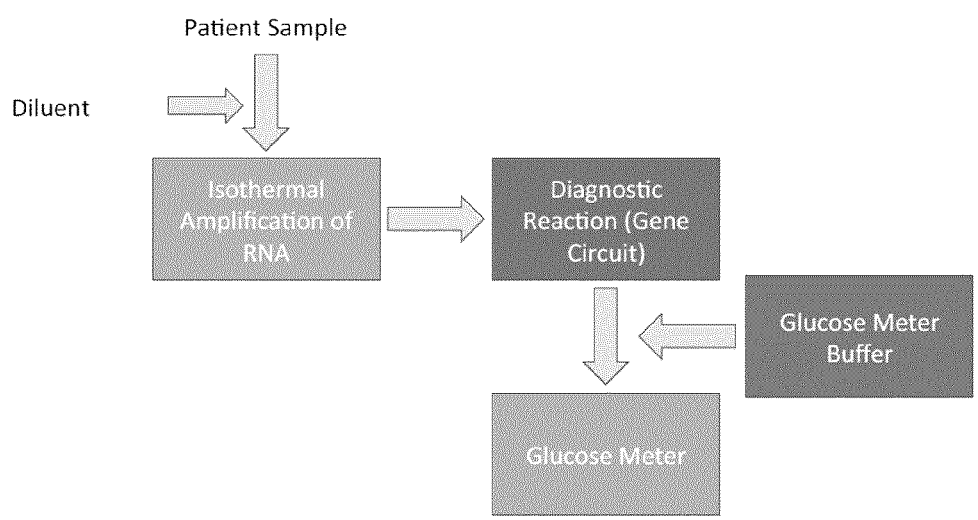
FIG. 9 shows one embodiment of a method for detecting a target analyte in a patient sample. Optionally, a glucose meter buffer (5× 0.1 M NaCl, 0.1 M sodium phosphate, 0.05% tween-20, pH 7.3) is added to the reaction volume before detecting glucose using the glucose meter.

As shown in FIG. 8, a simulated diagnostic reaction using a cell-free system and toehold switch E resulted in the production of glucose in response to the target analyte (RNA trigger sequence E) that was readily detected using a portable blood glucose meter.

Example 3

Multiplexed Detection of Target Analytes in a Single Reaction Volume

A common reaction mixture containing two different toehold switches was assembled and aliquoted into replicates. The first set of triplicate reactions were then incubated without trigger and were used to normalize data against background signal. As shown in FIG. 10A, the next set of triplicate reactions received trigger E RNA and produced a low, but significant, increase in glucose. The third set of triplicate reactions received trigger G RNA to produce a greater and distinct amount of glucose.

More than one target analyte can therefore be distinguished using a single reaction with two different gene circuits. This demonstrates a simulated diagnostic application where more than one pathogen/analyte is distinguished using a single reaction with glucose outputs that are dependent on which RNA input is present.

FIG. 10B shows the results from similar experiments performed to characterize the multiplexed detection of two different target RNA sequences using two different glucose-generating enzymes. Each target activates the production of a different enzyme, and each enzyme generates a distinct amount of glucose. Target A triggers the production of a lactase, while target B triggers the production of a trehalase. All toehold switches were present in all reactions, with the only difference being the target added. The values in FIG. 10B are shown after subtraction of background signal, determined by measuring a control reaction without any target present. Samples were incubated at 37° C. for 1 hour. Glucose concentration was measured using a blood glucose meter.

FIG. 10C shows results generated using a single enzyme (a trehalase) for the detection of two different targets in a multiplex reaction rather than different enzymes for each target. Each target activates production of the same enzyme, but at different rates due to differences in the kinetics of the toehold switches. This results in distinct rates of glucose production depending on the target(s) present, including a stronger signal when both are present. All toehold switches were present in all reactions, with the only difference being the target(s) added. Values are shown after subtraction of background signal, determined by measuring a control reaction without any target present. Samples were incubated at 37° C. for 1 hour. Glucose concentration was measured using a blood glucose meter. As shown in FIG. 10C, samples containing target A, target B or targets A+B were readily distinguished.

Example 4

Figure 11:
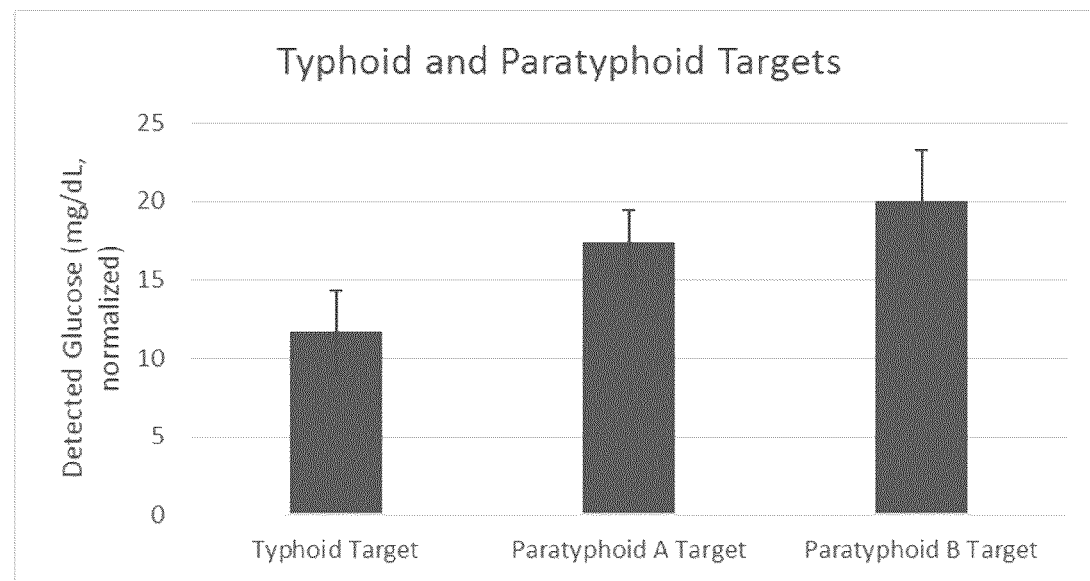
FIG. 11 shows the use of a synthetic biological circuit that produces glucose for the detection of typhoid and paratyphoid targets.

Use of Synthetic Biological Circuits for the Detection of Typhoid and Paratyphoid Targets Toehold switches were designed to detect RNA sequences from typhoid, paratyphoid A, and paratyphoid B respectively. All toehold switches were configured to activate production of a trehalase enzyme for glucose generation. FIG. 11 shows preliminary data before optimization of switch DNA concentration and substrate to enhance and differentiate the generated signals, but a clear increase can be seen in all three cases. The data presented in FIG. 11 is not a multiplexed experiment, as only one toehold switch was present in each reaction. Values are shown after subtraction of background signal, determined by measuring a control reaction without any target present. Samples were incubated at 37° C. for 1 hour. Glucose concentration was measured using a blood glucose meter.

Example 5

Glucose Meter Mediated Diagnostic Workflow

Figure 12:
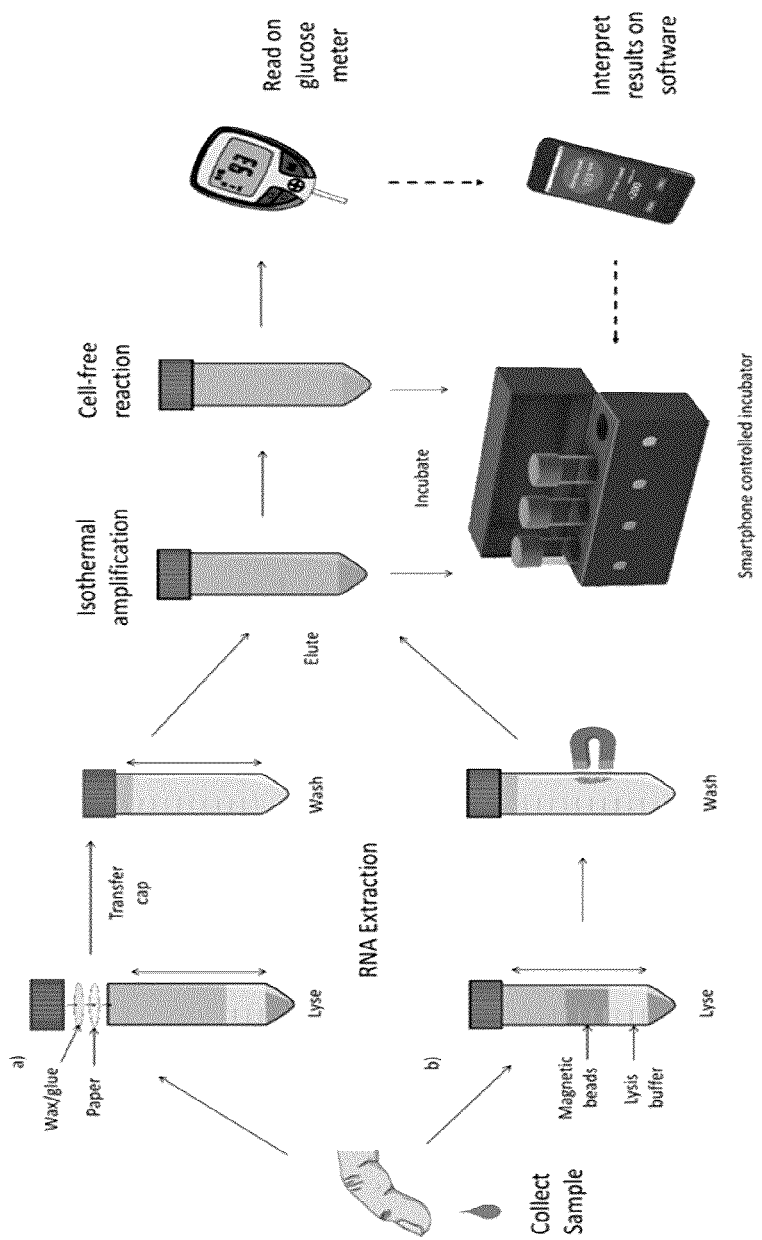
FIG. 12 shows an exemplary glucose meter mediated workflow for diagnostic applications.

FIG. 12 shows an exemplary (but not limited to) glucose meter mediated diagnostics workflow. The general process of the proposed workflow follows 6 steps; Step 1—Sample collection, Step—2 RNA Extraction, Step 3—Isothermal amplification, Step 4—Cell-free reaction coupled with target-specific sensors that produce glucose in the presence of the target RNA, Step 5—Sample analysis on a glucose meter, and Step 6—the interpretation of results on custom software. Preferred embodiments of the methods described herein may include one or more of steps shown in FIG. 12 for which optional details are set out below.

Step 1: Sample Collection

The sample may be a patient blood sample or other biological sample.

Step 2: RNA Extraction

Various RNA extraction methods can be used such as a) paper-based extraction or b) magnetic bead extraction.

For paper-based extraction, a paper or membrane is attached to the inside of the cap of a tube using glue or wax. Lysis buffer is added to the sample to a final concentration of 1×. The tube is inverted, and the cap incubated with the extract for 1 min, after which the cap is transferred to another tube with wash buffer, and inverted continuously for 1 min. Finally, the cap is transferred to another tube that contains the isothermal reaction mixture. The tube is inverted and incubated with the mixture for another minute to elute the RNA.

For magnetic bead extraction, similar to the paper-based extraction method, lysis buffer is added to the sample to a final concentration of 1×. A solution containing magnetic beads will be then added to the sample, and mixed until uniform. The magnetic beads, and the nucleic acid bound to them, will be collected to the side of the tube using a magnet, and the lysis waste removed. The subsequent wash step will proceed similarly; with the wash buffer being added to the tube, the tube being shaken to homogenize the mixture, and with the magnetic beads once again being collected to the side of the tube using a magnet. As a final step, the RNA will be eluted from the beads into either water or directly into an isothermal amplification reaction mixture.

Step 3) Isothermal Amplification Reaction

If the target that is intended to be detected is found at low concentrations in the initial sample, it may be necessary to amplify the target RNA to a level that is compatible with the sensor. This will be done using an isothermal or near-isothermal amplification method, such as NASBA. The reaction incubation may be performed in a smartphone-controlled incubator.

Step 4) Cell-Free Reaction

The amplified RNA may then be added directly to cell-free reactions, which will contain sensors designed to express significant levels of trehalase only upon recognition of the target RNA. The trehalase will then catalyse the breakdown of the trehalose (supplied in the reaction) into glucose monomers. The reaction incubation may be performed in a smartphone-controlled incubator.

Step 5) Glucose Meter

Cell free reactions may then be tested on glucose strips, with the expectation that positive samples would yield a significant increase in glucose levels that could be read by a glucose meter.

Step 6) Analyze Results

A smartphone app may be used to interpret the glucose meter data (and optionally forward data to family doctor or to public health surveillance programs, +/− anonymously). This is optionally the same app that controls the incubator used in Steps 3) and 4)

Example 7

Nucleic Acid Extraction Using Recycling Cap Paper Extraction (ReCap) or Magnetic Beads Experiments were performed to investigate capturing nucleic acids from samples using paper or membrane. Zou et al. (2017) (hereby incorporated by reference) previously described the use of cellulose paper for nucleic acid purification.

The paper is adhered to the cap of a tube, and the nucleic acids are captured in the initial lysis stage. The cap with the captured nucleic acids is then transferred to a wash tube which removes any potential inhibitors of downstream reactions, which includes any residual glucose from the blood sample. The final stage involves eluting the nucleic acids into an amplification reaction.

Experiments were also performed to investigate capturing nucleic acids from samples using magnetic extraction.

Materials and Reagents

Buffers were used at a final concentration of 1× during the lysis step. 4× buffers allow for more sample to be added at the lysis step.

TABLE 2

Buffers for ReCap and for Magnetic Bead extraction: A) and B) list different compositions of extraction buffer #3 used for lysis. C) lists the composition of the wash buffer. Note that these buffers are used for both ReCap extraction and the magnetic bead-based extraction. For RNA extraction the buffers were modified to contain 0.5% v/v of Murine RNase Inhibitor (NEB).

| Reagent | Final Conc | | Initial Conc | | To Add | | Final Volume | |
|---|---|---|---|---|---|---|---|---|
| A) - 1× Extraction Buffer #3 | | | | | | | | |
| Tween-20 | 1% | v/v | 100% | v/v | 0.5 | mL | 50 | mL |
| EDTA | 5 | mM | NA | | 0.07306 | g | 50 | mL |
| NaCl | 100 | mM | NA | | 1.1688 | g | 50 | mL |
| Guanidine Hydrochloride | 1.5 | M | 8 | M | 9.375 | mL | 50 | mL |
| Tris pH8 | 50 | mM | 1 | M | 2.5 | mL | 50 | mL |
| H2O | | | to adj volume | | 37.625 | ml | | |
| | | | | | 50 | mL | | |
| B) - 4× Extraction Buffer #3 | | | | | | | | |
| Tween-20 | 4% | v/v | 100% | v/v | 2 | mL | 50 | mL |
| EDTA | 20 | mM | NA | | 0.29224 | g | 50 | mL |
| NaCl | 400 | mM | NA | | 1.1688 | g | 50 | mL |
| Guanidine Hydrochloride | 6 | M | 8 | M | 37.5 | mL | 50 | mL |
| Tris pH8 | 200 | mM | 1 | M | 10 | mL | 50 | mL |
| H2O | | | to adj volume | | 0.5 | ml | | |
| | | | | | 50 | mL | | |
| C) - Wash Buffer | | | | | | | | |
| Tris pH8 | 0.01 | M | 1 | M | 0.5 | mL | 50 | mL |
| Tween-20 | 0.10% | v/v | 100% | v/v | 0.05 | mL | 50 | mL |
| NFH2O | | | | | 49.45 | mL | 50 | mL |
| | | | | total | 50 | mL | | |

ReCap Fabrication

Instead of utilizing paper as either loose paper disks or dipsticks, tubes were utilized that have the paper adhered to the inside of the cap of the tube. This method was tested using both Whatman filter paper and Polyethersulfone (PES) membrane, utilizing both hot glue and paraffin wax to adhere the paper/membrane. Theoretically, this method can be adopted for any type and volume of tube with a cap (50 mL, 15 mL, 2 mL, 1.5 mL, strip PCR tubes, etc.)

The following protocol steps were used:
1. Set up Lysis, Wash and Elution tubes. If the buffers contain RNase I Inhibitor, keep the tubes on ice.
    a. Set up the lysis tube in a ReCap tube, add extraction buffer at the appropriate concentration so that the final concentration of the extraction buffer will be 1× after the addition of your sample.
    b. In the Wash tube, add 200 μL of Wash buffer
    c. In the Elution tube, set up an amplification reaction mix (for example—a PCR reaction or a NASBA amplification reaction). This tube should be kept on ice.
2. Lysis:
    a. In a ReCap tube combine sample to be extracted with extraction buffer to a final concentration of 1×.
    b. Mix by Inverting the tube for 1 minute.
    c. Collect any liquid that may remain adhered to the lid by gently tapping the tube on a counter.
3. Wash
    a. Transfer the ReCap lid to the Wash tube
    b. Mix by inverting the tube for 1 minute
    c. Collect any liquid that may remain adhered to the lid by gently tapping the tube on a counter.
4. Elution
    a. Transfer the ReCap lid to the elution tube
    b. Mix by inverting the tube for 1 minute.
    c. Collect any liquid that may remain adhered to the lid by gently tapping the tube on a counter.
    d. Remove ReCap lid for a conventional lid. This is important as any reaction that requires significant heat may melt the adhesive used in ReCap.
5. Amplification
    a. PCR: Run reactions in a standard PCR protocol. For example, ReCap was assayed using NEB Q5 Polymerase Protocol as listed in Table 3.

b. Isothermal Reaction: ReCap was assayed using a NASBA reaction as listed in Table 4.

TABLE 3

PCR amplification protocol.
Standard Q5 PCR Reaction

| | | |
|---|---|---|
| 5X Q5 Reaction Buffer | 10 | μL |
| GC enhancer | 10 | μL |
| 10 mM dNTPs | 1 | μL |
| 10 uM fwd primer | 2.5 | μL |
| 10 uM rev primer | 2.5 | μL |
| template | 1 | μL |
| Q5 polymerase | 0.5 | μL |
| NF H20 | 22.5 | μL |
| final volume | 50 | μL |

| Conditions | temp | time |
|---|---|---|
| Denaturation | 98 | 2 min |
| 30 Cycles | 98 | 15 sec |
|  | 55 | 30 sec/kb |
|  | 72 | 1 min |
| Final Extension | 72 | 10 min |
| Hold | 4 | hold |

TABLE 4

Isothermal NASBA protocol
25 μL NASBA Reaction

| | Final Composition | | Vol to add | |
|---|---|---|---|---|
| Reaction buffer | 0.335 | % | 8.38 | μL |
| Nucleotide Mix | 0.165 | % | 4.13 | μL |
| RNase Inhibitor | 0.005 | % | 0.13 | μL |
| Primer 1 (500 nM) | 0.05 | μM | 0.13 | μL |
| Primer 2 (500 nM) | 0.05 | μM | 0.13 | μL |
| NF H20 | 0.035 | % | 0.88 | μL |
| Enzyme Mix | 0.25 | % | 6.25 | μL |
| RNA amplicon* | 0.2 | % | 5.00 | μL |
| total volume | | | 25 | μL |

NASBA reactions were run at 62° C. for 2 mins, at which point the enzyme mix was added and the reaction was run at 41° C. for 1 hr.

Figure 13:
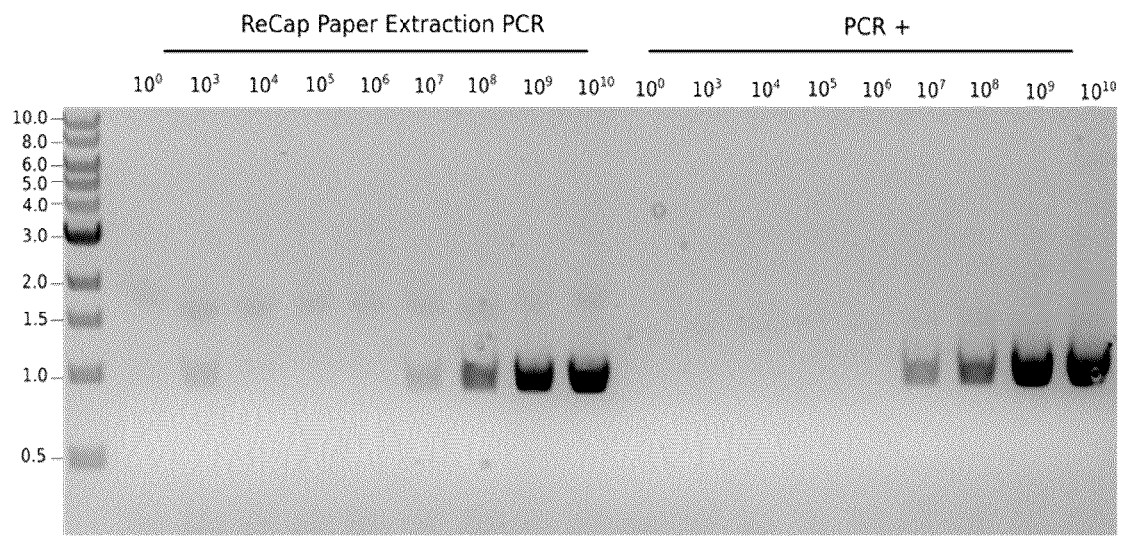
FIG. 13 shows the results of ReCap paper extraction PCR and control PCR reactions.

ReCap Extraction and Amplification $10^0$ to $10^{10}$ copies of mRFP1 plasmid DNA template were spiked into extraction buffer, bound to paper, washed, and eluted into 50 μL PCR reactions. In the PCR+ control $10^0$ to $10^{10}$ copies of DNA template were added directly to the Q5 polymerase PCR reaction. 5 μL of the PCR products were run on a 1% agarose gel. As shown in FIG. 13, the ReCap method is able to capture nucleic acids down to the PCR sensitivity limit ($10^7$ copies of DNA).

Figure 14:
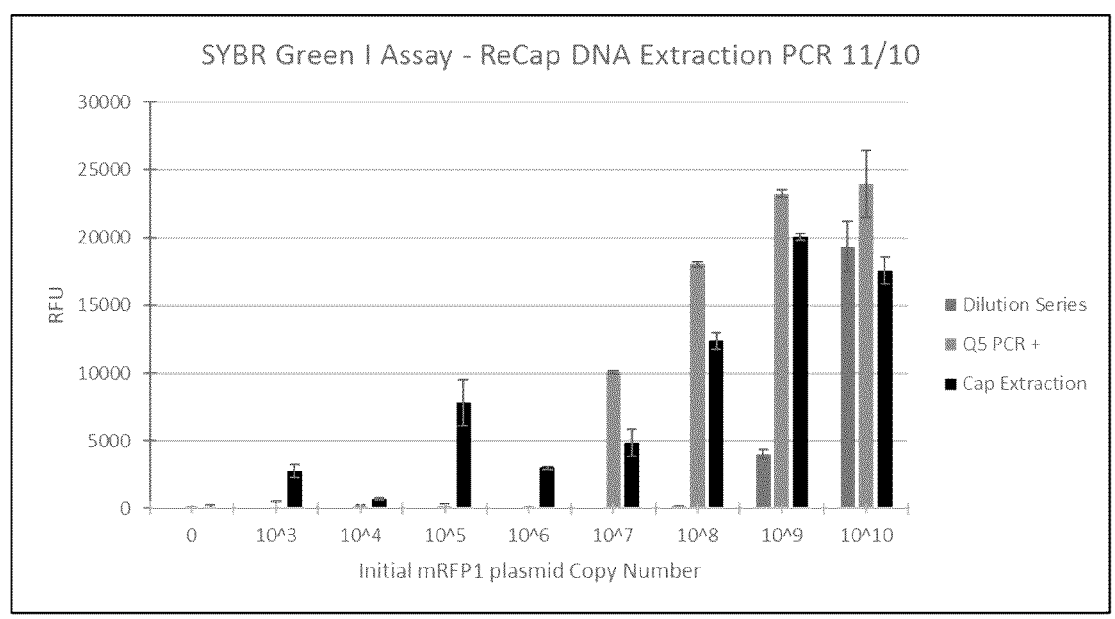
FIG. 14 shows the results of a SYBR Green I Assay with ReCap paper extraction PCR.

SYBR Green I dye was added to the same reactions as shown in FIG. 13 and endpoint fluorescence measured using a standard plate reader with 0-$10^{10}$ copies of mRFP1. Results are shown in FIG. 14. As SYBR Green I is a fluorescent intercalating dye for dsDNA, Relative Fluorescence Units (RFUs) can be used to compare yields of dsDNA from different amplification reactions.

Magnetic Bead Extraction and Amplification

As an alternative to ReCap extraction, experiments were performed using magnetic bead-based extraction methods with magnetic beads from the Genesig Easy DNA/RNA Extraction kit (Tube 3), along with the buffers (listed in Table 2) from the ReCap paper extraction method. The following protocol steps were used:

1. Lysis
   a. Add sample and extraction buffer to a final concentration of 1x. Add an equal volume of Tube 3 (solution with Magnetic beads) as supplied in the kit.
   b. Shake the tube and wait for 15 minutes
   c. Magnetize and remove all liquid
2. Wash
   a. Add 200 μL of Wash buffer.
   b. Shake the tube and wait 30 seconds
   c. Magnetize and remove all liquid.
3. Elute
   a. Elute in the appropriate volume of water or amplification mix.

Figure 15:
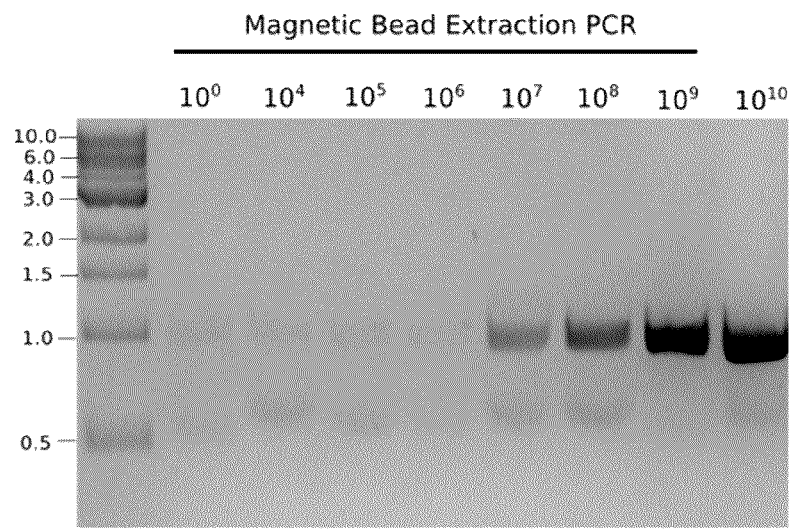
FIG. 15 shows the results of magnetic bead extraction PCR.

Similar to the experiments performed for ReCap, $10^0$-$10^{10}$ copies of mRFP1 plasmid were added to 50 μL of extraction buffer, bound to magnetic beads, washed, and eluted into Q5 polymerase PCR buffer. The reaction products were run on a 1% agarose gel. As shown in FIG. 15, successful extraction using magnetic beads was seen within the PCR detection range ($10^7$-$10^{10}$).

Isothermal Amplification and Cell-Free Reaction

The amplification methods used for amplifying nucleic acids prior to detection using a synthetic circuit are preferably isothermal or near-isothermal (i.e. NASBA). Experiments were performed using Zika sensors (see Pardee et al. 2016, hereby incorporated by reference) in order to investigate the use of ReCap paper extraction with NASBA.

$10^{10}$ copies of Zika virus Trigger 3 RNA were spiked into 50 μL of extraction buffer, bound to paper, washed, and eluted into a 25 μL NASBA reaction. NASBA reactions were then added in a 1:7 ratio to 1.8 μL cell-free reactions containing Zika toehold sensors that produce the LacZ enzyme only upon recognition of the Zika RNA trigger. The LacZ enzyme produced then cleaves a substrate (CPRG) to produce chlorophenol red, which can be detected at 570 nM.

Figure 16:
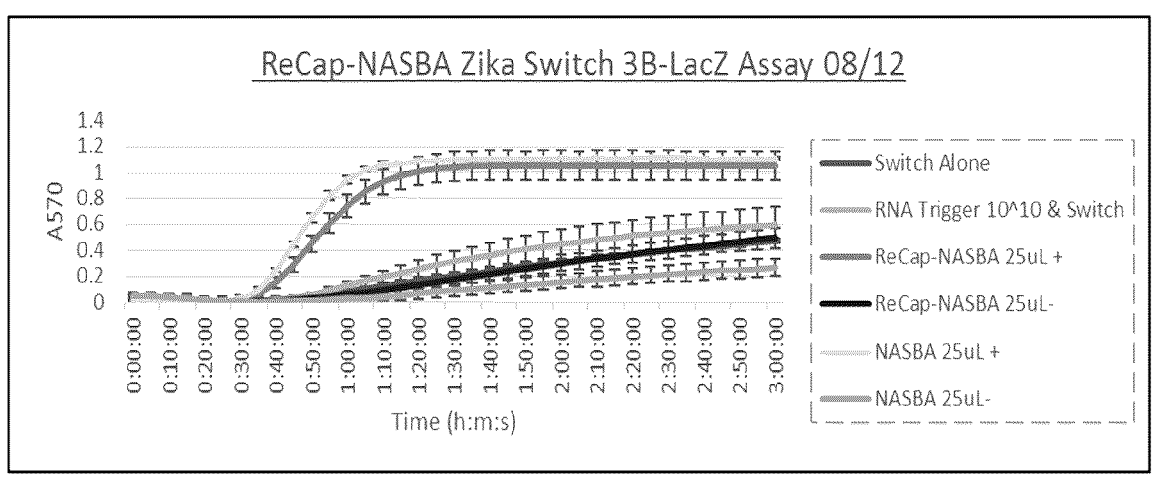
FIG. 16 shows the results of ReCap RNA extraction followed by NASBA amplification.

As shown in FIG. 16, ReCap extraction is compatible with NASBA amplification and cell-free toehold sensing.

Example 8

Environmental Sensing of Mercury Using Synthetic Biological Circuits

Glucose meter mediated sensing using synthetic biological circuits may also be used for the detection of environmental analytes, such as metals. Specifically, the sensors and methods may be used for environmental monitoring and remediation, as well as for detecting/prospecting for valuable metals such as precious or rare earth elements.

Current methods of sensing environmental mercury rely on expensive equipment such as atomic absorption (AA) spectroscopy, High Pressure Liquid Chromatography (HPLC) and Mass Spectroscopy MS in order to determine levels of mercury contamination present in water, tissue and soil samples.

For the purposes of detecting mercury, samples may include water, tissue, and soil samples. The extraction method depends on the type of sample. For example, for soil-based extraction a combination of centrifugation and filtration methods are common (see for example Reis et al. 2014). For extraction of mercury from tissue samples, samples may be lyophilized and microwaved (see for example Hinojosa Reyes et al. 2009)

For extraction of mercury from water, samples are most commonly subjected to a method of coagulation/filtration.

As shown in FIG. 17, extracted samples may be tested with gene circuit-based sensors that produce either green fluorescence or trehalase enzyme in response to the presence of mercury.

Mercury sensors are designed using the Tn21 Promoter, which is bound and sequestered by a MerR repressor in the absence of mercury. Once mercury is present, the repressor unbinds and exposes the Tn21 promoter, allowing for transcription of downstream genes by the E. coli RNA polymerase (RNAP). Sensor design is tested using deGFP fluorescent reporter before coupling the Tn21-MerR gene regulatory system with a Trehalase enzyme for use with a glucose meter. The Trehalase enzyme catalyses the breakdown of trehalose into glucose monomers in the presence of mercury. The produced glucose levels are measured on glucose test strips with a glucose meter. Optionally, a smartphone app assists with interpreting the results from the glucose meter and with data analysis.

All publications, biological sequences or sequence identifiers, patents and patent applications are herein incorporated by reference in their entirety to the same extent as if each individual publication, biological sequence, patent or patent application was specifically and individually indicated to be incorporated by reference in its entirety.

REFERENCES

Hinojosa Reyes et al. Robust microwave-assisted extraction protocol for determination of total mercury and methylmercury in fish tissues. *Analytica Chimica Acta* Volume 631, Issue 2, 12 Jan. 2009, Pages 121-128.

Lan et al. Transforming the blood glucose meter into a general healthcare meter for in vitro diagnostics in mobile health. *Biotechnol Adv.* 2016, 34(3), 331-341.

Pardee et al. Paper-based Synthetic Gene Networks. *Cell*, 2014, 159: 940-954.

Pardee et al. Rapid, Low-Cost Detection of Zika Virus Using Programmable Biomolecular Components. *Cell.* 2016 May 19; 165(5):1255-66.

Reis et al. Extraction of mercury water-soluble fraction from soils: An optimization study. *Geoderma* Volume 213, January 2014, Pages 255-260.

Roelof Van der Meer and Belkin. Where microbiology meets microengineering: design and applications of reporter bacteria. *Nat Rev Microbiol.*, 2010, Jull 8(7)511-522).

Wang et al. Multiplex detection of nucleic acids using a low cost microfluidic chip and a personal glucose meter at the point-of-care. *Chem. Commun.*, 2014, 50, 3824-3826.

Wedekind et al. Metalloriboswitches: RNA-based inorganic ion sensors that regulate genes. *The Journal of Biological Chemistry* 292, 9441-9450 Jun. 9, 2017.

Yu Xiang and Yi Lu. Using personal glucose meters and functional DNA sensors to quantify a variety of analytical targets *Nat Chem.* 2011 Jul. 24; 3(9): 697-703.

Zhou et al. Metal Sensing by DNA. *Chem. Rev.*, 2017, 117 (12), pp 8272-8325.

Zou et al. Nucleic acid purification from plants, animals and microbes in under 30 seconds. *PLoS Biol* 15(11): e2003916. Nov. 21, 2017.

The invention claimed is:

1. A method for modifying glucose in response to a target nucleic acid molecule in a sample, the method comprising:
   (i) contacting the sample with a synthetic biological circuit within a cell-free system reaction volume, the reaction volume present in a container, wherein the synthetic biological circuit comprises a DNA molecule comprising a promoter operably linked to a DNA molecule encoding an enzyme whose expression modifies the level of glucose in the reaction volume and the target nucleic acid molecule activates the synthetic biological circuit in the reaction volume to regulate translation of a mRNA molecule encoding the enzyme to modify the level of glucose in the reaction volume, and
   (ii) detecting glucose in the cell-free system reaction volume using a glucose meter thereby detecting the target nucleic acid molecule in the sample,
   wherein the synthetic biological circuit further comprises a riboregulator that controls translation of the mRNA molecule encoding the enzyme, wherein the riboregulator recognizes the target nucleic acid molecule and the target nucleic acid molecule is a trigger for the riboregulator such that binding of the target nucleic acid molecule to the riboregulator changes the conformation of the riboregulator thereby permitting translation of the mRNA encoding the enzyme in the synthetic biological circuit, and
   wherein the cell-free system comprises a substrate that is acted on by the enzyme to generate glucose and
   i) the substrate is trehalose and the enzyme is trehalase;
   ii) the substrate is maltose and the enzyme is maltase;
   iii) the substrate is cellobiose and the enzyme is cellobiase;
   iv) the substrate is starch and the enzyme is amylase;
   v) the substrate is lactose and the enzyme is lactase (beta-galactosidase);
   vi) the substrate is sucrose and the enzyme is invertase or sucrase;
   vii) the substrate is glucose and the enzyme is glucose dehydrogenase; or
   viii) the substrate is glucose-6-phosphate or glucose-1-phosphate and the enzyme is glucose 6-phosphatase.

2. The method of claim 1, wherein the riboregulator is a toehold switch.

3. The method of claim 1, wherein the cell-free system is freeze-dried and rehydrated by contact with the sample and/or a reaction buffer.

4. The method of claim 1, comprising detecting a level of glucose in the cell-free system reaction volume thereby quantifying a level of the target analyte in the sample.

5. The method of claim 1, comprising detecting glucose in the cell-free system reaction volume using a glucose test strip.

* * * * *